US012431248B2

(12) United States Patent
Gill et al.

(10) Patent No.: US 12,431,248 B2
(45) Date of Patent: Sep. 30, 2025

(54) SYSTEM AND METHOD FOR INTER-DEVICE ARRHYTHMIA DETECTION AND CONFIRMATION

(71) Applicant: TC1 LLC, Wilmington, DE (US)

(72) Inventors: Jong Gill, Valencia, CA (US); Nima Badie, Oakland, CA (US); Kyungmoo Ryu, Palmdale, CA (US); Avi Fischer, New Rochelle, NY (US); Philip B. Adamson, Austin, TX (US)

(73) Assignee: TC1 LLC, Wilmington, DE (US)

( * ) Notice: Subject to any disclaimer, the term of this patent is extended or adjusted under 35 U.S.C. 154(b) by 0 days.

(21) Appl. No.: 18/325,147

(22) Filed: May 30, 2023

(65) Prior Publication Data

US 2023/0411019 A1 Dec. 21, 2023

Related U.S. Application Data

(60) Provisional application No. 63/353,046, filed on Jun. 17, 2022.

(51) Int. Cl.
*G16H 50/30* (2018.01)
*A61B 5/00* (2006.01)
(Continued)

(52) U.S. Cl.
CPC ......... *G16H 50/30* (2018.01); *A61B 5/02028* (2013.01); *A61B 5/0215* (2013.01);
(Continued)

(58) Field of Classification Search
CPC ..... G16H 50/30; A61B 5/686; A61N 1/36585
See application file for complete search history.

(56) References Cited

U.S. PATENT DOCUMENTS 9,049,995 B2 6/2015 Blomqvist et al.
9,114,264 B2 8/2015 Karst et al.
(Continued)

OTHER PUBLICATIONS

Reiter et al "Influence of Intracardiac Pressure on Spontaneous Ventricular Arrhythmias in Patients With Systolic Heart Failure Insights From the REDUCEhf Trial" Circ Arrhythm Electrophysiol; 2023 (8 pages).

(Continued)

*Primary Examiner* — Carl H Layno
*Assistant Examiner* — Maria Catherine Anthony
(74) *Attorney, Agent, or Firm* — Dean D. Small; The Small Patent Law Group, LLC

(57) ABSTRACT

System for arrhythmia detection and confirmation includes implantable medical device (IMD) having a sensing circuit for sensing cardiac activity (CA) for one or more cardiac cycles and generating one or more CA signals. An implantable pressure sensor (IPS) includes IPS sensing circuit for sensing pressure during the one or more cardiac cycles and generating one or more pressure signals. IMD and IPS include communications circuits for communicating with each other and/or an external device. One or both of IMD or IPS includes memory for storing program instructions and processor(s) for analyzing one of the CA or pressure signals, for one or more cardiac cycles, to detect a candidate arrhythmia. In response to detecting candidate arrhythmia, the processor(s) obtain another one of CA or pressure signals for cardiac cycles corresponding to the one or more cardiac cycles, and confirm or deny candidate arrhythmia based on the other one of the signals.

20 Claims, 11 Drawing Sheets

120 130 108 101 106 100 104 External Device 138 122 123 150 136 134 132 112

(51) Int. Cl.

| | |
|---|---|
| ***A61B 5/02*** | (2006.01) |
| ***A61B 5/0215*** | (2006.01) |
| ***A61N 1/365*** | (2006.01) |
| *A61N 1/37* | (2006.01) |

(52) U.S. Cl.

CPC .......... *A61B 5/686* (2013.01); *A61N 1/36585* (2013.01); *A61N 1/3704* (2013.01)

(56) References Cited

U.S. PATENT DOCUMENTS

| | | | | |
|---|---|---|---|---|
| 9,179,846 | B2 | 11/2015 | Hou et al. | |
| 9,265,964 | B2 | 2/2016 | Karst et al. | |
| 9,301,702 | B2 * | 4/2016 | Ngo | A61B 5/7282 |
| 9,566,442 | B2 | 2/2017 | Ngo et al. | |
| 9,687,656 | B2 | 6/2017 | Wenzel et al. | |
| 10,166,397 | B2 | 1/2019 | Farazi et al. | |
| 10,709,341 | B2 | 7/2020 | White et al. | |
| 2009/0204163 | A1 * | 8/2009 | Shuros | A61N 1/36585 607/23 |
| 2019/0091478 | A1 * | 3/2019 | Wisnoskey | A61N 1/36564 |
| 2019/0381321 | A1 | 12/2019 | Hopper | |
| 2020/0375490 | A1 * | 12/2020 | Herrmann | A61B 5/363 |
| 2023/0109023 | A1 * | 4/2023 | Park | A61N 1/365 607/62 |

OTHER PUBLICATIONS

Petrucci et al "Right Ventricular Pressure Changes During Induced Ventricular Tachycardias Predict Clinical Symptoms of Cerebral Hypoperfusion: Implications for a Reduction of Unnecessary, Painful ICD Shocks" Journal of Cardiovascular Electrophysiology vol. 20, No. 3, Mar. 2009 (8 pages).

* cited by examiner

SYSTEM AND METHOD FOR INTER-DEVICE ARRHYTHMIA DETECTION AND CONFIRMATION

CROSS-REFERENCE TO RELATED APPLICATIONS

This application claims priority to U.S. Provisional Patent Application No. 63/353,046, filed 17 Jun. 2022, titled "SYSTEM AND METHOD FOR INTER-DEVICE ARRHYTHMIA DETECTION AND CONFIRMATION". The subject matter of the provisional application is expressly incorporated herein by reference in its entirety.

BACKGROUND

Embodiments of the present disclosure generally relate to implantable medical devices and methods, and more particularly to communications between implanted sensors and medical devices within a patient for detecting and confirming arrhythmia.

Proper arrhythmia diagnosis in cardiac rhythm management (CRM) devices, such as implantable cardiac defibrillators, pacemakers, cardiac resynchronization therapy (CRT) devices, pacemakers, implantable cardiac monitors, and the like is critical as the device provides therapies, often in real-time or near-real time, in response to the diagnosis. As such, the diagnosis may have a significant influence on the clinical management of patients. In some cases, however, painful shocks can be administered when the physiologic condition, such as an arrhythmia, is well-tolerated, and may be managed by a therapy that is less impactful to the patient's quality of life.

Passive implantable medical sensors are currently available to monitor certain physiologic conditions, such as blood pressure. One example is a passive pulmonary arterial (PA) pressure sensor, or passive PAP sensor. However, passive implantable medical sensors require active patient participation in order to collect the physiologically relevant data and to make the data available to a clinician. For example, passive PA pressure sensors utilize an external device, outside of the patient body, for supplying energy to the sensors to power the generation and communication of the physiological data. Consequently, the system requires initial patient training and periodic reminders for the patient to utilize the external device for data collection and communication. The physiologic data is analyzed to improve the patient outcome, such as by modifying a treatment of the patient based on the physiologic data generated by the passive sensor.

Because user interaction is required to utilize the external device to activate the passive sensor, the sensor may only collect data when it is convenient for the patient. Therefore, there may be significant delays between a time at which a physiologic condition of the patient changes and a time in which physiologic data is collected by the passive implantable medical sensor and communicated for analysis. The physiologically relevant data may not be timely collected by the passive sensor nor readily available to other implanted devices such as pacemakers and CRT devices, and thus the sensor data cannot be relied upon to determine real-time treatment. Accordingly, the use of such externally powered devices may be limited to long-term tracking of chronic, but not imminently life-threatening, conditions.

A need remains for a system and method for sensing and analyzing physiologic data from an implantable medical sensor for real-time analysis in combination with an implantable medical device to confirm an arrhythmia and improve patient outcomes.

SUMMARY

In accordance with embodiments herein, a system for arrhythmia detection and confirmation comprises an implantable medical device (IMD) and an implantable pressure sensor (IPS). The IMD includes a sensing circuit and an IMD communications circuit. The sensing circuit is configured to sense cardiac activity (CA), on-demand and in real-time, for one or more cardiac cycles and to generate one or more CA signals based on the CA. The IMD communications circuit is configured to communicate with at least one of an implantable sensor or an external device. The IPS comprises an IPS sensing circuit and an IPS communications circuit. The IPS sensing circuit is configured to sense pressure, on-demand and in real-time, during the one or more cardiac cycles and to generate one or more pressure signals based on the pressure. The IPS communications circuit is configured to communicate with at least one of the IMD or the external device. At least one of the IMD or IPS further comprises a memory configured to store program instructions and one or more processors that, when executing the program instructions, are configured to analyze one of the CA or pressure signals, for the one or more cardiac cycles, to detect a candidate arrhythmia. In response to the detection of the candidate arrhythmia, the one or more processors obtain another one of the CA or pressure signals for cardiac cycles corresponding to the one or more cardiac cycles, and confirm or deny the candidate arrhythmia based on the other one of the CA or pressure signals.

Optionally, wherein the one or more processors and memory are housed in the IMD and the one or more processors are configured to direct the IMD communications circuit to transmit, to at least one of the IPS communications circuit or the external device, a request for the pressure signals, receive the pressure signals from at least one of the IPS communications circuit or the external device, and analyze the pressure signals, for the one or more cardiac cycles, to confirm or deny the candidate arrhythmia.

Optionally, wherein the one or more processors and memory are housed in the IPS and the one or more processors are configured to direct the IPS communications circuit to transmit, to at least one of the IMD communications circuit or the external device, a request for the CA signals, receive the CA signals from at least one of the IMD communications circuit or the external device, and analyze the CA signals, for the one or more cardiac cycles, to confirm or deny the candidate arrhythmia.

Optionally, the one or more processors is further configured to analyze both of the CA and pressure signals to determine a CA-based rate and to determine a pressure-based rate and confirm or deny the candidate arrhythmia based on a comparison of the CA and pressure-based rates. Optionally, the one or more processors are further configured to compare the pressure signals, for the one or more cardiac cycles, relative to a template for a normal sinus rhythm to determine when the pressure signals indicate a pressure-indicated arrhythmia and confirm or deny the candidate arrhythmia based on the comparison of the pressure signals.

Optionally, the one or more processors is further configured to analyze the CA signals to identify the candidate arrhythmia to be a ventricular tachycardia, compare the pressure signals, for the one or more cardiac cycles, relative to a template for a normal sinus rhythm to determine when the pressure signals have morphological features that correspond to the normal sinus rhythm, and determine the candidate arrhythmia to be an atrial fibrillation and not the ventricular tachycardia initially identified based on the CA signals based on the comparison of the pressure signals.

Optionally, the one or more processors is further configured to determine when one or more features of the pressure signals positively or negatively exceed at least one corresponding threshold associated with hemodynamic instability and identify the candidate arrhythmia to be an atrial fibrillation when all or a subset of the one or more features of the pressure signals positively or negatively exceed the one or more corresponding threshold.

Optionally, in response to confirming the candidate arrhythmia based on the CA signals and denying the candidate arrhythmia based on the pressure signals, the one or more processors is further configured to increase at least one sensitivity setting associated with sensing the cardiac activity. Optionally, the one or more processors is further configured to analyze additional CA signals that are sensed by the IMD sensing circuit, the additional CA signals based on the increased at least one sensitivity setting, and confirm or deny the candidate arrhythmia based on the analysis of the additional CA signals.

Optionally, in response to the one or more processors confirming the candidate arrhythmia associated with the pressure signals, the one or more processors is further configured to identify the candidate arrhythmia as a stable arrhythmia if a magnitude of one or more features of the pressure signals is greater than a hemodynamic threshold, and identify the candidate arrhythmia as an unstable arrhythmia if the magnitude of the one or more features of the pressure signals is less than the hemodynamic threshold. Optionally, the one or more features of the pressure signals can include at least one of i) pulse pressure, ii) systolic pressure, iii) diastolic pressure, or iv) $dP/dt_{max}$.

Optionally, in response to the one or more processors confirming the candidate arrhythmia associated with the pressure signals, the one or more processors is further configured to identify the candidate arrhythmia as a stable arrhythmia if a variability of one or more features of the pressure signals is greater than a hemodynamic threshold, and identify the candidate arrhythmia as an unstable arrhythmia if the variability of the one or more features of the pressure signals is less than the hemodynamic threshold.

Optionally, the one or more processors is further configured to detect a pause in response to analyzing the CA signals. In response to detecting a pause, analyze the pressure signals to determine whether ventricular contraction is present or absent. and in response to the ventricular contraction being present, reject a diagnosis of pause.

Optionally, wherein in response to the confirmation of the candidate arrhythmia, the one or more processors is further configured to treat the candidate arrhythmia. Optionally, wherein the treatment of the candidate arrhythmia includes delivery of i) ATP, ii) a low voltage shock, iii) a medium voltage shock, or iv) a high voltage shock.

In accordance with embodiments herein, a computer implemented method for detecting an arrhythmia comprises sensing cardiac activity (CA), for one or more cardiac cycles, at a sensing circuit within an implantable medical device (IMD). One or more CA signals are generated based on the CA. Pressure is sensed, during the one or more cardiac cycles, at an implantable pressure sensor (IPS). A pressure signal is generated based on the pressure. Under control of one or more processors configured with executable instructions, one of the CA or pressure signals, for the one or more cardiac cycles, are analyzed to detect a candidate arrhythmia, another one of the CA or pressure signals are obtained for cardiac cycles corresponding to the one or more cardiac cycles, and the candidate arrhythmia is confirmed or denied based on the other one of the CA or pressure signals.

Optionally, the method further comprises transmitting, from an IMD communications circuit within the IMD, a request for the pressure signals from the IPS. The pressure signals for the one or more cardiac cycles are received at the IMD communications circuit. The pressure signals for the one or more cardiac cycles are analyzed, under control of the one or more processors housed in the IMD, to confirm or deny the candidate arrhythmia.

Optionally, the method further comprises transmitting, from an IPS communications circuit within the IPS, a request for the CA signals from the IMD. The CA signals are received at the IPS communications circuit. The CA signals for the one or more cardiac cycles are analyzed, under control of one or more processors being housed in the IPS, to confirm or deny the candidate arrhythmia.

Optionally, the method further comprises analyzing both of the CA and pressure signals to determine a CA-based rate and to determine a pressure-based rate. The candidate arrhythmia is confirmed or denied based on a comparison of the CA and pressure-based rates.

Optionally, the method further comprises comparing the pressure signals, for the one or more cardiac cycles, relative to a template for a normal sinus rhythm to determine when the pressure signals indicate a pressure-indicated arrhythmia, and confirming or denying the candidate arrhythmia based on the comparison of the pressure signals.

Optionally, the method further comprises determining when one or more features of the pressure signals positively or negatively exceed at least one corresponding threshold associated with hemodynamic instability, and identifying the candidate arrhythmia to be an atrial fibrillation when all or a subset of the one or more features of the pressure signals positively or negatively exceed the one or more corresponding threshold.

Optionally, in response to confirming the candidate arrhythmia based on the CA signals and denying the candidate arrhythmia based on the pressure signals, the one or more processors is further configured to increase at least one sensitivity setting associated with sensing the cardiac activity.

DETAILED DESCRIPTION

Figure 1:
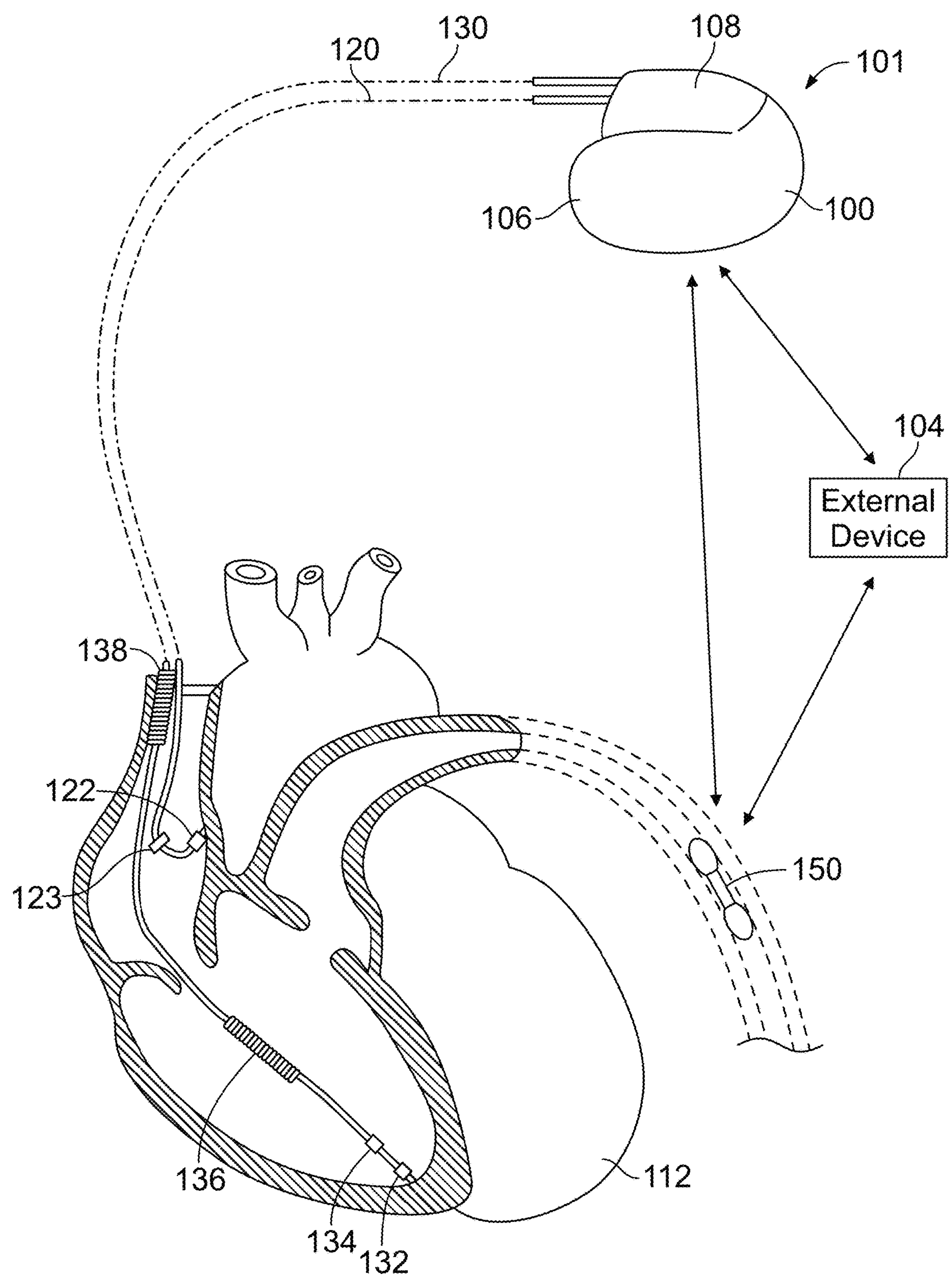
FIG. 1 illustrates a system that includes an implantable medical device (IMD), an implantable pressure sensor (IPS), and an optional external device (ED) implemented in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Embodiments may be implemented in connection with one or more implantable medical devices (IMDs). Non-limiting examples of IMDs include one or more of implantable leadless monitoring and/or therapy devices, and/or alternative implantable medical devices. For example, the IMD may represent a cardiac monitoring device, cardioverter defibrillator, pacemaker, cardiac rhythm management device, leadless pacemaker, leadless implantable medical device (LIMD), and the like.

Additionally or alternatively, the IMD may be a subcutaneous IMD that includes one or more structural and/or functional aspects of the device(s) described in U.S. Pat. No. 10,765,860, titled "Subcutaneous Implantation Medical Device With Multiple Parasternal-Anterior Electrodes"; U.S. Pat. No. 10,722,704, titled "Implantable Medical Systems And Methods Including Pulse Generators And Leads"; U.S. Pat. No. 11,045,643, titled "Single Site Implantation Methods For Medical Devices Having Multiple Leads", which are hereby incorporated by reference in their entireties. Further, one or more combinations of IMDs may be utilized from the incorporated patents and applications identified herein in accordance with embodiments herein.

In accordance with embodiments herein, the methods, devices, and systems may be implemented in connection with the systems and methods described in U.S. published application US20210020294A1, entitled "METHODS DEVICE AND SYSTEMS FOR HOLISTIC INTEGRATED HEALTHCARE PATIENT MANAGEMENT" filed Jul. 16, 2020, which is incorporated herein by reference in its entirety. In accordance with embodiments herein, the methods, devices, and systems may be implemented in connection with the communications systems and methods described in U.S. patent application Ser. No. 17/820,654, filed on Aug. 18, 2022, titled "System and Method for Intra-Body Communication of Sensed Physiologic Data", which is incorporated herein by reference in its entirety. In accordance with embodiments herein, the methods, devices, and systems may be implemented in connection with those described in U.S. Pat. No. 11,559,241, filed on Oct. 1, 2019, titled "Methods and Systems for Reducing False Declarations of Arrythmias", which is incorporated herein by reference in its entirety.

All references, including publications, patent applications and patents, cited herein are hereby incorporated by reference to the same extent as if each reference were individually and specifically indicated to be incorporated by reference and were set forth in its entirety herein.

Terms

The terms "abnormal", "arrhythmic", and "arrhythmia" are used to refer to events, features, and characteristics of, or appropriate to, an unhealthy or abnormal functioning of the heart.

The terms "cardiac activity signal", "cardiac activity signals", "CA signal" and "CA signals" (collectively "CA signals") are used interchangeably throughout to refer to measured signals indicative of cardiac activity by a region or chamber of interest. For example, the CA signals may be indicative of impedance, electrical or mechanical activity by one or more chambers (e.g., left or right ventricle, left or right atrium) of the heart and/or by a local region within the heart (e.g., impedance, electrical or mechanical activity at the AV node, along the septal wall, within the left or right bundle branch, within the purkinje fibers). The cardiac activity may be normal/healthy or abnormal/arrhythmic. An example of CA signals includes electrogram (EGM) signals. Electrical based CA signals refer to an analog or digital electrical signal recorded by two or more electrodes, where the electrical signals are indicative of cardiac activity. Heart sound (HS) based CA signals refer to signals output by a heart sound sensor such as an accelerometer, where the HS based CA signals are indicative of one or more of the S1, S2, S3 and/or S4 heart sounds. Impedance based CA signals refer to impedance measurements recorded along an impedance vector between two or more electrodes, where the impedance measurements are indicative of cardiac activity.

The term "PA" shall mean pulmonary artery. The term "PAP" shall mean pulmonary arterial pressure.

The terms "pressure signal" and "PAP signal" are used interchangeable throughout to refer to measured signals indicative of pulmonary arterial pressure measured within the pulmonary artery.

The terms "high-voltage shock" and "HV shock" refer to defibrillation stimulus delivered at an energy level sufficient to terminate a defibrillation episode in a heart, wherein in some embodiments the energy level is defined in Joules to be approximately 40 J or more and/or the energy level is defined in terms of voltage to be approximately 750V or more.

The terms "low voltage shock", "low voltage stimulation", "LV shock" and the like, refer to stimulus delivered at an energy level below an MV shock energy level, and above a pacing pulse energy level, wherein the energy level is defined in Joules, maximum charge voltage and/or pulse width. In connection with an IMD having a transvenous lead, the foregoing terms refer to stimulation that has an energy level that is no more than approximately 20V, in some embodiments to be between approximately 5V-15V and in other embodiments, to be between 7V-10V.

The terms "medium-voltage shock" and "MV shock" refer to defibrillation stimulus delivered at an energy level sufficient to terminate a defibrillation episode in a heart, wherein the energy level is defined in Joules, pulse width, and/or maximum charge voltage. An MV shock from an IMD with a transvenous lead will have a different maximum energy and/or charge voltage than an MV shock from a subcutaneous IMD with a subcutaneous lead. In connection with an IMD having a transvenous lead, the terms medium voltage shock and MV shock refer to defibrillation stimulation that has an energy level that is no more than approximately 25 J, and more preferably approximately 15-25 J and/or has a maximum voltage of no more than approximately 500V, preferably between approximately 100-475V and more preferably between approximately 400-475V. In connection with an IMD having a subcutaneous lead (e.g., parasternal or otherwise), the terms medium voltage shock and MV shock refer to defibrillation stimulation that has an energy level that is no more than approximately 40 J, and more preferably approximately 30-40 J, and/or has a maximum voltage of no more than approximately 35 V, preferably between approximately 25-35 V and more preferably between approximately 20-35 V.

The term "marker" refers to data and/or information identified from CA signals and pressure signals that may be presented as graphical and/or numeric indicia indicative of one or more features within the CA or pressure signals and/or indicative of one or more episodes exhibited by the cardiac events. Non-limiting examples of markers may include R-wave markers, noise markers, activity markers, interval markers, refractory markers, P-wave markers, T-wave markers, PVC markers, sinus rhythm markers, AF markers, VA markers (e.g., VF, VT), and other arrhythmia markers.

The terms "normal sinus rhythm", "NSR", and "NSR template" are used to refer to events, features, and characteristics of, or appropriate to, a heart's healthy or normal functioning. The NSR template can include one or more of the events, features, and characteristics.

The terms "treatment", "arrhythmia treatment", "in connection with treating a heart condition" and similar phrases, as used herein include, but are not limited to, delivering an electrical stimulation to a heart condition. The treatment, such as of ventricular arrhythmias (VA), including ventricular tachycardia (VT) and ventricular fibrillation (VF), can include, but are not limited to, delivering an electrical stimulation to treat a heart condition. By way of example, treating a heart condition may include, in whole or in part, i) identifying a ventricular arrhythmia and/or an atrial arrhythmia occurring over one or more heart beats; ii) determining CA and/or pressure-based rates; iii) comparing signal features and/or morphology of CA and/or pressure signals to NSR template(s); iv) confirming or denying an arrhythmia identified by an arrhythmia detection process; v) adjusting IMD sensitivity setting(s) to increase the sensitivity while collecting CA; vi) determining hemodynamic stability of the patient, such as by analysis of pressure signals; and/or vii) delivering a therapy based on one or more of the comparisons and the hemodynamic stability.

The term "POC" shall mean point-of-care. The terms "point-of-care" and "POC", when used in connection with medical diagnostic testing, shall mean methods and devices configured to provide medical diagnostic testing at or near a time and place of patient care. The time and place of patient care may be at an individual's home, such as when providing "at home" point of care solutions. The time and place of patient care may be at a physician's office or other medical facility, wherein one or more medical diagnostic tests may be performed on-site at a time of or shortly after a patient visit and collection of a patient sample. The POC may implement the methods, devices and systems described in one or more of the following publications, all of which are expressly incorporated herein by reference in their entireties: U.S. Pat. No. 6,786,874, entitled "APPARATUS AND METHOD FOR THE COLLECTION OF INTERSTITIAL FLUIDS" issued Sep. 7, 2004; U.S. Pat. No. 9,494,578, entitled "SPATIAL ORIENTATION DETERMINATION IN PORTABLE CLINICAL ANALYSIS SYSTEMS" issued Nov. 15, 2016; and U.S. Pat. No. 9,872,641, entitled "METHODS, DEVICES AND SYSTEMS RELATED TO ANALYTE MONITORING" issued Jan. 23, 2018.

The terms "stable", "hemodynamically stable", "unstable", "stability", and similar terms shall mean an instant or near-real-time determination of the hemodynamic stability of the patient. Pressure signals may be used to determine whether the arrhythmia episode is stable and tolerable, in which case a perfusion to the brain is still maintained and treatment of the patient may be applied at a lower intensity, such as ATP, or withheld. If the pressure signals indicate that the arrhythmia episode is unstable, MV and/or HV treatment may be indicated.

The term "obtains", "obtaining", "collect", and "collecting", as used in connection with data, signals, information and the like, can be used interchangeably herein and include at least one of i) accessing memory of an external device or remote server where the data, signals, information, etc., are stored, ii) receiving the data, signals, information, etc., over a wireless communications link between the IMD and a local external device, and/or iii) receiving the data, signals, information, etc., at a remote server over a network connection. The obtaining operation, when from the perspective of an IMD and/or implantable sensor, may include sensing new signals in real time, and/or accessing memory to read stored data, signals, information, etc., from memory within the IMD. The obtaining operation, when from the perspective of a local external device, includes receiving the data, signals, information, etc., at a transceiver of the local external device where the data, signals, information, etc., are transmitted from an IMD and/or a remote server. The obtaining operation may be from the perspective of a remote server, such as when receiving the data, signals, information, etc., at a network interface from a local external device and/or directly from an IMD. The remote server may also obtain the data, signals, information, etc., from local memory and/or from other memory, such as within a cloud storage environment and/or from the memory of a workstation or clinician external programmer. The IMD and implantable sensor may also obtain data, signals, and information from each other in response to a request or a triggering event.

The terms "processor," "a processor", "one or more processors" and "the processor" shall mean one or more processors. The one or more processors may be implemented by one, or by a combination of more than one implantable medical device, a wearable device, a local device, a remote device, a server computing device, a network of server computing devices and the like. The one or more processors may be implemented at a common location or at distributed locations. The one or more processors may implement the various operations described herein in a serial or parallel manner, in a shared-resource configuration and the like.

The term "health care system" refers to a system that includes equipment for measuring health parameters, and communication pathways from the equipment to secondary devices. The secondary devices may be at the same location as the equipment, or remote from the equipment at a different location. The communication pathways may be internal within the patient, wired, wireless, over the air, cellular, in the cloud, etc. In one example, the healthcare system provided may be one of the systems described in U.S. published application US20210020294A1, entitled "METHODS DEVICE AND SYSTEMS FOR HOLISTIC INTEGRATED HEALTHCARE PATIENT MANAGEMENT" filed Jul. 16, 2020, which is incorporated herein by reference in its entirety. Other patents that describe example monitoring systems include U.S. Pat. No. 6,572,557; entitled SYSTEM AND METHOD FOR MONITORING PROGRESSION OF CARDIAC DISEASE STATE USING PHYSIOLOGIC SENSORS, filed Dec. 21, 2000, to Tchou et al.; U.S. Pat. No. 6,480,733 entitled METHOD FOR MONITORING HEART FAILURE filed Dec. 17, 1999, to Turcott; U.S. Pat. No. 7,272,443 entitled SYSTEM AND METHOD FOR PREDICTING A HEART CONDITION BASED ON IMPEDANCE VALUES USING AN IMPLANTABLE MEDICAL DEVICE, filed Dec. 14, 2004, to Min et al; U.S. Pat. No. 7,308,309 entitled DIAGNOSING CARDIAC HEALTH UTILIZING PARAMETER TREND ANALYSIS, filed Jan. 11, 2005, to Koh; and U.S. Pat. No. 6,645,153 entitled SYSTEM AND METHOD FOR EVALUATING RISK OF MORTALITY DUE TO CONGESTIVE HEART FAILURE USING PHYSIOLOGIC SENSORS, filed Feb. 7, 2002, to Kroll et. al., the entire contents of which are incorporated in full herein.

The term "real-time" shall mean a time frame contemporaneous with normal or abnormal episode occurrences. For example, a real-time process or operation would occur during or immediately after (e.g., within seconds after) a cardiac event, a series of cardiac events, an arrhythmia episode, and the like. For example, the term "real-time" may refer to a time period substantially contemporaneous with an event of interest. The term "real-time," when used in connection with collecting and/or processing data utilizing an IMD or IPS, shall refer to processing operations performed substantially contemporaneous with a physiologic event of interest experienced by a patient. By way of example, in accordance with embodiments herein, pressure and/or cardiac activity signals are analyzed in real time (e.g., during a cardiac event or within a few minutes after the cardiac event).

The term "on-demand" shall mean at any time that the system automatically determines that a measurement is warranted and without any need for patient action or intervention. As one example, an implantable sensor will collect pressure measurements "on-demand" automatically and in real-time in response to a data collection instruction from an IMD. As another example, an implantable sensor will collect pressure measurements "on-demand" automatically and in real-time in response to a data collection instruction from an external device such as a bedside monitor, smart phone, physician's programmer and the like. As another example, an implantable sensor will collect pressure measurements "on-demand" automatically and in real-time in response to a data collection schedule stored at the sensor, IMD or ED.

LIMD

Additionally or alternatively, the IMD may be a leadless implantable medical device (LIMD) that includes one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

S-IMD

Additionally or alternatively, the IMD may be a subcutaneous IMD that includes one or more structural and/or functional aspects of the device(s) described in U.S. Pat. No. 10,765,860, entitled "Subcutaneous Implantation Medical Device With Multiple Parasternal-Anterior Electrodes" issued Sep. 8, 2020; U.S. Pat. No. 10,722,704, entitled "Implantable Medical Systems And Methods Including Pulse Generators And Leads" issued Jul. 28, 2020; and U.S. Pat. No. 11,045,643, entitled "Single Site Implantation Methods For Medical Devices Having Multiple Leads", issued Jun. 29, 2021, which are hereby incorporated by reference in their entireties. Further, one or more combinations of IMDs may be utilized from the above incorporated patents and applications in accordance with embodiments herein.

ICM

Additionally or alternatively, the IMD may be a leadless cardiac monitor (ICM) that includes one or more structural and/or functional aspects of the device(s) described in U.S. Pat. No. 9,949,660, entitled "METHOD AND SYSTEM TO DISCRIMINATE RHYTHM PATTERNS IN CARDIAC ACTIVITY" issued Apr. 24, 2018, which is expressly incorporated herein by reference.

The implantable medical sensor disclosed herein may implement one or more structural and/or functional aspects of the device(s) described in U.S. patent application Ser. No. 16/194,103, filed Nov. 16, 2018, and entitled "Wireless Sensor for Measuring Pressure;" U.S. patent application Ser. No. 14/733,450, filed Jun. 8, 2015, now U.S. Pat. No. 10,143,388, and entitled "Method of Manufacturing Implantable Wireless Sensor for In Vivo Pressure Measurement;" U.S. patent application Ser. No. 12/612,070, filed Nov. 4, 2009, and entitled "Method of Manufacturing Implantable Wireless Sensor for In Vivo Pressure Measurement," now U.S. Pat. No. 9,078,563; U.S. patent application Ser. No. 11/204,812, filed on Aug. 16, 2005 and entitled "Method of Manufacturing Implantable Wireless Sensor for In Vivo Pressure Measurement," now U.S. Pat. No. 7,621,036; U.S. patent application Ser. No. 11/157,375, filed Jun. 21, 2005 and entitled "Implantable Wireless Sensor for In Vivo Pressure Measurement," which are expressly incorporated herein by reference.

PIMD (Passive Implantable Medical Device)

Embodiments may be implemented in connection with one or more PIMDs. Non-limiting examples of PIMDs may include passive wireless sensors used by themselves, or incorporated into or used in conjunction with other implantable medical devices (IMDs) such as cardiac monitoring devices, pacemakers, cardioverters, cardiac rhythm management devices, defibrillators, neurostimulators, leadless monitoring devices, leadless pacemakers, replacement valves, shunts, grafts, drug elution devices, blood glucose monitoring systems, orthopedic implants, and the like. For example, the PIMD may include one or more structural and/or functional aspects of the device(s) described in U.S. Pat. No. 9,265,428 entitled "Implantable Wireless Sensor", U.S. Pat. No. 8,278,941 entitled "Strain Monitoring System and Apparatus", U.S. Pat. No. 8,026,729 entitled "System and Apparatus for In-Vivo Assessment of Relative Position of an Implant", U.S. Pat. No. 8,870,787 entitled "Ventricular Shunt System and Method", and U.S. Pat. No. 9,653,926 entitled "Physical Property Sensor with Active Electronic Circuit and Wireless Power and Data Transmission", which are all hereby incorporated by reference in their respective entireties.

System Overview

In accordance with new and unique aspects herein, methods and devices are described that determine that a patient is experiencing a candidate arrhythmia, such as a VA, VF, VT, or AF based on cardiac activity signals collected and generated by an IMD and/or pressure signals collected and generated by an implantable pressure sensor. The methods and devices can confirm the candidate arrhythmia based on data from one or both devices. Further, if the candidate arrhythmia is only detected based on the pressure signals, the methods and devices can adjust IMD sensitivity settings, such as by increasing the sensitivity, to confirm the candidate arrhythmia.

The methods and devices can also determine the hemodynamic stability (e.g., stable, unstable) associated with the pressure signals. By determining the hemodynamic stability, a technical advantage is realized as therapy can be selected to address the arrhythmia the patient is currently experiencing without overtreating the patient.

FIG. 1 illustrates a system 101 that includes an implantable medical device (IMD) 100, an implantable pressure sensor (IPS) 150, and an external device 104 implemented in accordance with embodiments herein. The IMD 100 and the IPS 150 are implanted within the body of a patient. The external device 104 is outside of the patient body. The external device 104 may be a programmer, an external defibrillator, a workstation, a portable computer (e.g., laptop or tablet computer), a personal digital assistant, a cell phone (e.g., smartphone), a bedside monitor, a remote care server, and the like. The external device 104 can provide multiple functions, including performing the function of a one-way and/or bidirectional bridge/gateway for transmitting or relaying requests, messages, CA and IPS signals, and the like between the IMD 100 and the IPS 150, as well as assessing the appropriateness of therapies delivered by the IMD 100. The IMD 100 may represent a cardiac monitoring device, a pacemaker, a cardioverter, a cardiac rhythm management device, a defibrillator, a neurostimulator, a leadless monitoring device, a leadless pacemaker, and the like, implemented in accordance with one embodiment of the present invention. The IMD 100 may be a dual-chamber stimulation device capable of treating both fast and slow arrhythmias with stimulation therapy, including cardioversion, defibrillation, anti-tachycardia pacing and pacing stimulation, as well as capable of detecting heart failure, evaluating its severity, tracking the progression thereof, and controlling the delivery of therapy and warnings in response thereto.

The IMD 100 includes a housing 106 that is joined to a header assembly 108 that holds receptacle connectors connected to a right ventricular lead 130 and an atrial lead 120, respectively. The atrial lead 120 includes a tip electrode 122 and a ring electrode 123. The right ventricular lead 130 includes an RV tip electrode 132, an RV ring electrode 134, an RV coil electrode 136, and an SVC coil electrode 138. The leads 120 and 130 detect intracardiac electrogram (IEGM) signals that are processed and analyzed as described herein, and also deliver therapies as described herein.

The IMD 100 may be implemented as a full-function biventricular pacemaker, equipped with both atrial and ventricular sensing and pacing circuitry for four chamber sensing and stimulation therapy (including both pacing and shock treatment). Optionally, the IMD 100 may further include a coronary sinus lead with left ventricular electrodes. The IMD 100 may provide full-function cardiac resynchronization therapy. Alternatively, the IMD 100 may be implemented with a reduced set of functions and components. For instance, the IMD may be implemented without ventricular sensing and pacing.

The IPS 150 is configured to be implanted at a location remote from the electrodes of the leads 120 and 130. The IPS 150 may be implanted in a blood vessel, such as an artery or vein. In some embodiments, the IPS 150 is implanted within the pulmonary artery (PA). The IPS 150 may be anchored to the vessel wall of a blood vessel using one or more expandable loop wires. The diameter of each loop should be larger than the diameter of target blood vessel in order to provide adequate anchoring force. Optionally, instead of the loop wire, the IPS 150 may be attached to the end of a self-expandable stent and deployed into the blood vessel through a minimally invasive method. This method may be preferable over the loop wire(s) in situations in which strong anchoring is needed. It should be understood that the sensor may be implanted and fixed in place utilizing other configurations. The IPS 150, when disposed within the PA, is configured to sense pressure (e.g., blood pressure), and to generate signals indicative of the pressure.

Figure 2:
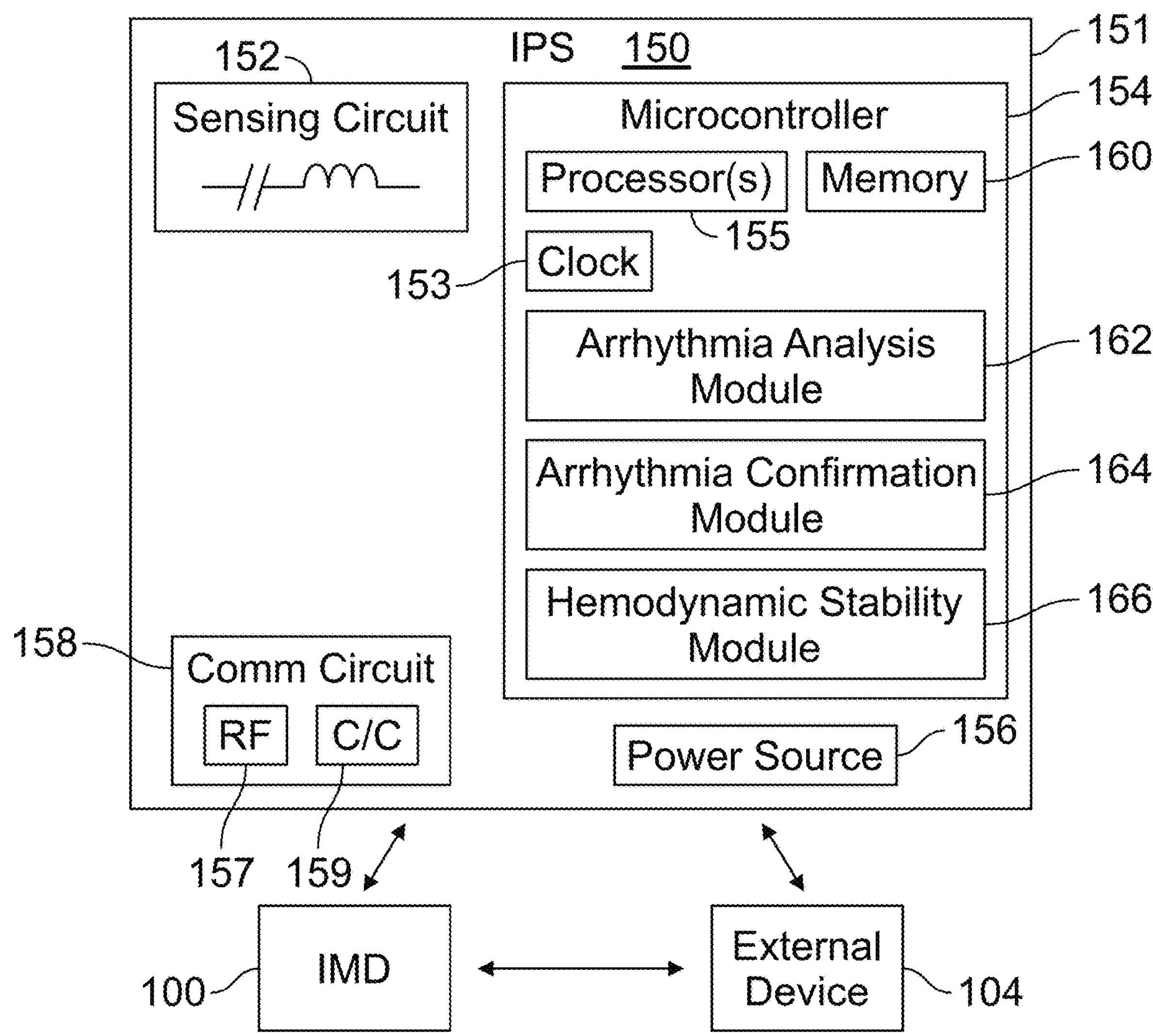
FIG. 2 illustrates a block diagram of the system of FIG. 1 formed in accordance with embodiments herein, showing components of the IPS in accordance with embodiments herein.

FIG. 2 illustrates a block diagram of the system 101 formed in accordance with embodiments herein, showing components of the IPS 150. The IPS 150 comprises a sensing circuit 152, a controller 154, a power source 156, a communications circuit 158 and a memory 160. By way of example, the IPS 150 may be implemented in accordance with one or more aspects of the sensors described in U.S. Provisional application 63/262,115, filed Oct. 5, 2021 and titled "SYSTEM AND METHOD FOR INTRA-BODY COMMUNICATION OF SENSED PHYSIOLOGIC DATA", the complete subject matter of which is incorporated by reference in its entirety. The controller 154 includes one or more processors 155. The one or more processors 155 are operably coupled to the memory 160. The IPS 150 includes a housing 151 that holds and encapsulates the sensing circuit 152, the controller 154, the power source 156, the communications circuit 158, and the memory 160, to protect these components from the harsh organic environment of the body. The housing 151 may be hermetically sealed.

The sensing circuit 152 is configured to sense and collect pressure data (e.g. pulse pressure) and to generate pressure signal(s) indicative of the pressure data. For example, the sensing circuit 152 of an implantable pressure sensor (e.g., IPS 150) senses pressure, on-demand and in real-time, during one or more cardiac cycles and generates a pressure signal based on the sensed pressure. The signals generated by the sensing circuit 152 represent electrical signals. Electrical parameters of the signals, such as voltage, current, capacitance, inductance or resistance, may vary based on a level of the pressure. The sensing circuit 152 includes one or more sensing elements that sense the pressure and circuitry that generates the electrical signals indicative of the pressure.

The controller 154 may be implemented as a microcontroller unit or another processor configuration. The controller 154 performs at least some of the operations described herein to collect real-time on-demand measurements by generating physiologic data and can communicate the physiologic data to at least a second device, without requiring patient interaction or external energy delivery at the time of data generation and/or communication. The controller 154 represents hardware circuitry that includes and/or is connected with the one or more processors 155 (e.g., one or more microprocessors, integrated circuits, field programmable gate arrays, etc.).

The controller 154 includes and/or is connected to the memory 160, which is a tangible and non-transitory computer-readable storage medium. The memory 160 stores program instructions (e.g., software) that are executed by the one or more processors 155 to perform the operations of the IPS 150 described herein. The memory 160 additionally may store the physiologic data (e.g., pressure signals) that is generated by the sensing circuit 152 and the CA signals generated and transmitted by the IMD 100. The memory 160 may store the physiologic data until the IPS 150 transmits the physiologic data to the IMD 100 and/or the external device 104, and/or operate as a memory loop by deleting the oldest data as new data is acquired. For example, the controller 154 can prepare and send pressure data collected by the IPS 150, such as over time (e.g., 10 seconds, 30 seconds, one minute, etc.) to the IMD 100.

The IPS 150 can include processing modules that are included and/or stored in the controller 154 and/or memory 160. An arrhythmia analysis module 162 can analyze and/or compare the pressure signals and/or CA signals from the IMD 100, for one or more cardiac cycles, to detect/determine a candidate arrhythmia. The arrhythmia analysis module 162 can compare, as discussed further below, CA and pressure-based rates, the pressure data collected by the IPS 150 and/or the CA signals received from the IMD 100 to normal sinus rhythm (NSR) template(s) (e.g., compare morphological features, predetermined thresholds, parameters, levels, and the like) that can be stored in the memory 160. The arrhythmia analysis module 162 can compare the pressure signals to one or more hemodynamic thresholds to determine whether a candidate arrhythmia is stable or unstable. An arrhythmia confirmation module 164 can, in response to information from the arrhythmia analysis module 162 and/or similar information from the IMD 100 (e.g., CA signals for cardiac cycles corresponding to the one or more cardiac cycles of the candidate arrhythmia), confirm or deny the candidate arrhythmia.

Once the candidate arrhythmia is confirmed, a hemodynamic stability module 166 can determine whether the pulse pressure signals generated by the IPS 150 indicate that the candidate arrhythmia is a hemodynamically stable VT or an hemodynamically unstable VT. For example, as discussed further below in at least FIGS. 4A-4C, the hemodynamic stability module 166 can compare amplitudes and/or pascal, pounds per square inch (psi), atmospheres (atm), etc., of pulse pressure over one or more heart beats to a threshold, and/or compare pulse pressure variability to a threshold. The hemodynamic stability processing can also be accomplished in the IMD 100.

In some embodiments, the controller 154 includes and/or is connected with an internal clock 153 or timer. The clock 153 may be used to cycle the IPS 150 between wake and sleep modes to conserve electrical energy. The controller 154 may refer to the clock 153 to determine when to activate the sensing circuit 152 to generate the signals indicative of the pressure according to a data collection schedule. For example, if the data collection schedule in the memory 160 indicates that new physiologic data should be generated at a specific time (e.g., 6 AM) of the current day, or, for example, at intervals such as every minute, two minutes, hour, etc., then the controller 154 can utilize the clock 153 to determine when it is the specific time to activate the sensing circuit 152 according to the schedule, such that the physiologic data is generated and collected in real-time at specific prescribed times.

The communications circuit 158 is operably connected to the controller 154 via conductive elements. The communications circuit 158 communicates with the IMD 100 and/or the external device 104. The communications circuit 158 may be communicatively connected to the IMD 100 via an intra-body bidirectional link, which enables the IPS 150 to transmit information (e.g., data) to the IMD 100 and receive information/requests from the IMD 100. The communications circuit 158 may include an RF module 157 and/or a conductive communication module 159. The RF module 157 includes an antenna for sending and receiving RF signals. In some cases, the processor(s) 155 can direct the IPS communications circuit 158 to transmit, to an IMD communications circuit 564 and/or communication modem 542 (both of FIG. 5) a request for the CA signals, and receive the CA signals. The conductive communication module 159 includes at least two spaced-apart electrodes, connected via a conductive wire or cable, that are powered to create a polarized electric field around the IPS 150.

The power source 156 supplies electrical energy to power the operations of the IPS 150. The power source 156 may include one or more secondary (e.g., rechargeable) batteries, one or more primary batteries, one or more capacitors, and/or associated circuitry, such as inductive coils, charging circuits, and the like.

In other embodiments, the IPS 150 can receive power from the IMD 100, such as through a wired connection. In some cases, the wired connection can also provide at least a portion of the communications between the IPS 150 and the IMD 100.

In operation, the controller 154 may directly convert, or manage conversion of, the signals from the sensing circuit 152 to digital physiologic data. The controller 154 may execute the program instructions stored in the memory 160 to activate the sensing circuit 152 to generate the signals indicative of the pressure. The controller 154 may activate the sensing circuit 152 on-demand in response to receiving a request (e.g., a data collection instruction) from another device, such as the IMD 100, or at a prescribed time according to a schedule stored in the memory 160. In some embodiments the controller 154 may activate the sensing circuit 152 on an on-going basis or near-on-going basis, acquiring and storing pressure data in the memory 160, such as in a loop, keeping the most recently acquired data. The controller 154 also executes the program instructions to convert the signals from the sensing circuit 152 to physiologic data indicative of the pressure. After converting, the controller 154 stores the physiologic data in the memory 160. In an embodiment, the controller 154 (e.g., the one or more processors 155 thereof) are configured to digitize the signals generated by the sensing circuit to form the physiologic data.

In some cases, the controller 154 directs the communications circuit 158 to transmit at least some of the physiologic data (e.g., pressure signal) stored in the memory 160 to the IMD 100. For example, the memory 160 may store the physiologic data that is recently converted and digitized until the controller 154 directs the communications circuit 158 to transmit the physiologic data. The communications circuit 158 may be directed to transmit the data in real-time in accordance with a predetermined schedule, on-demand in response to a request from the IMD 100 and or the external device 104, and/or in response to a stimulus, such as a determination by the controller 154 that the IPS 150 has detected a candidate arrhythmia, a determination by the controller 154 that the pressure has crossed a threshold value or has changed more than a threshold rate or extent, or the like.

In some embodiments, the IMD 100 can be utilized as a bridge component to relay communications between the IPS 150 and the external device 104. For example, the controller 154 may use the communication circuit 158 to transmit a message within the body of the patient to the IMD 100. Upon receipt, the IMD 100 may retransmit the message (or generate a new message that includes the content of the received message) to the external device 104. The IMD 100 may also relay messages received from the external device 104 to the IPS 150. Optionally, the IPS 150 may have sufficient onboard power to communicate information to the external device 104 and/or receive information from the external device 104 without utilizing the IMD 100 as a relay.

The IPS 150 produces pressure data along with a time stamp, and thus can be time synchronized relative to data collected by the IMD 100. The pressure measurements of the IPS 150 can be used to generate time-stamped or time synchronized pressure signal(s) over one or more cardiac cycles that can be compared to templates, thresholds, parameters, and/or CA signal data that may or may not be time-synchronized relative to the pressure signals.

In accordance with embodiments described herein, the intra-body communication between the IPS 150 and the IMD 100 provides various benefits. For example, the pressure is measured by the IPS 150 and the communications circuit 158 can transfer pressure data to the IMD 100 and receive data from the IMD 100, including CA signals and requests. In other embodiments, the communications circuit 158 can send other information to the IMD 100, such as a determination of a candidate arrhythmia based on pressure signals and/or CA signals, confirmation or denial of a candidate arrhythmia, a request for data and/or treatment of the patient, and the like.

In some embodiments, physiologic data, including in some cases the CA signals of the IMD 100, can be processed by the IPS 150, followed by communications/requests for treatment and/or confirmation or denial of certain arrhythmia conditions to the IPS 150. The IMD 100 may provide a treatment for the patient. When the IMD 100 is a CRT/pacemaker, the treatment may be stimulation therapy.

Communication between the IMD 100 and the IPS 150 enables autonomous and prompt adjustment of treatment parameters based on real-time feedback from the collected pressure. For example, in response to a change in the pressure, the IPS 150 (e.g., such as with arrhythmia analysis module 162, arrhythmia confirmation module 164, hemodynamic stability module 166) confirms or denies a candidate arrhythmia based on whether the pressure signals indicate arrhythmia. The timely confirmation/denial of the candidate arrhythmia enables appropriate treatment parameters to be provided by the IMD 100. Accordingly, the treatment is tailored and timely for the current patient conditions.

The IMD 100 is therefore able to more accurately apply the treatment parameters, relative to a conventional system that may rely on the CA data alone to determine the treatment parameters. No intervention is required to collect CA data and/or pressure data because the IMD 100 and IPS 150 may autonomously collect and communicate updated, real-time physiologic data and detected conditions to each other. The IMD 100 and IPS 150 can push data and/or request data to/from each other. The treatment parameters may be quickly modified because the IPS 150 can autonomously provide on-demand updates to the IMD 100. The IMD 100 can simply communicate a request or instruction to the IPS 150 whenever the IMD 100 wants to confirm a candidate arrhythmia. Optionally, the controller 154 may monitor the pressure and generate the pressure signal over time and determine when a value of the pressure signal crosses a designated threshold and/or changes at a rate or extent that is outside of an expected rate or extent of change. In response to making this determination, the IPS 150 may notify the IMD 100, and the IMD 100 can either confirm/deny the candidate arrhythmia, and/or take action to provide a treatment to the patient when the arrhythmia confirmation module 164 has confirmed or denied the candidate arrhythmia, thereby improving the patient outcome.

Accordingly, the IMD 100 delivers a particular treatment for the medical condition of arrhythmia (e.g., VA, VT, AF, etc.). The candidate arrhythmia is confirmed before treatment is administered to the patient. For example, cardiac activity data collected by the IMD 100 and pressure data collected by the IPS 150 can be used to confirm that an arrhythmia detected by one device is also detected by the other device. Further, once the candidate arrhythmia is confirmed, the hemodynamic stability of the patient can be determined based on pressure data collected by the IPS 150 to confirm that the level of treatment to be administered to the patient is appropriate to the patient's instant condition.

Further, the IMD 100 delivers the particular treatment which transforms the patient's heart from an arrhythmia state to a normal sinus rhythm state. As discussed in FIGS. 3A-4C, the IMD 100 monitors the CA signals and the IPS 150 monitors the pressure signals, one or both of the devices can determine various parameters such as CA and pressure-based rates, compare signal features and/or morphology to template(s), and/or determine the patient's instant hemodynamic stability and adjust the particular treatment applied by the IMD 100 as the patient's condition changes.

FIGS. 3A-3E illustrate computer-implemented methods for confirming a candidate arrhythmia in accordance with embodiments herein. The FIGS. 3A-3E further illustrate communication between the IMD 100 and the IPS 150. In some cases, processing to determine and/or confirm a candidate arrhythmia is accomplished with one or more processors of the IMD 100. In other cases, processing to determine and/or confirm a candidate arrhythmia is accomplished with one or more processors of the IPS 150, while in further cases one or more processors of both the IMD 100 and the IPS 150 can be used to determine and/or confirm a candidate arrhythmia. Steps that occur in more than one of the Figures are indicated with the same item number. In addition, it should be understood that when/after the IMD 100 treats the confirmed arrhythmia, the IMD 100 and IPS 150 can continue to collect and generate signals, analyze the signals to detect candidate arrhythmias, etc. In some embodiments, the communications between the IMD 100 and the IPS 150 are accomplished directly between the devices as discussed in FIGS. 3A-3E. In other embodiments, the communications between the IMD 100 and the IPS 150 are relayed by the external device 104. In yet further embodiments, some of the communications between the IMD 100 and the IPS 150 are accomplished directly between the devices, while other communications are relayed via the external device 104. Accordingly, the external device 104 can act as a gateway or bridge between the IMD 100 and the IPS 150 for some or all communications between the two implantable devices.

The operations of FIGS. 3A-3E may be implemented by hardware, firmware, circuitry and/or one or more processors housed partially and/or entirely within an IMD 100, an IPS 150, a local external device, remote server or more generally within a health care system. Optionally, the operations of FIGS. 3A-3E may be partially implemented by an IMD 100 and partially implemented by an IPS 150, a local external device, remote server or more generally within a health care system. For example, the IMD 100 includes IMD memory and one or more IMD processors, the IPS 150 includes IPS memory and one or more IPS processors, and further, each of the external devices/systems (e.g., local, remote or anywhere within the health care system) include external device memory and one or more external device processors.

Verification of IMD VT/VF Diagnosis

Figure 3A:
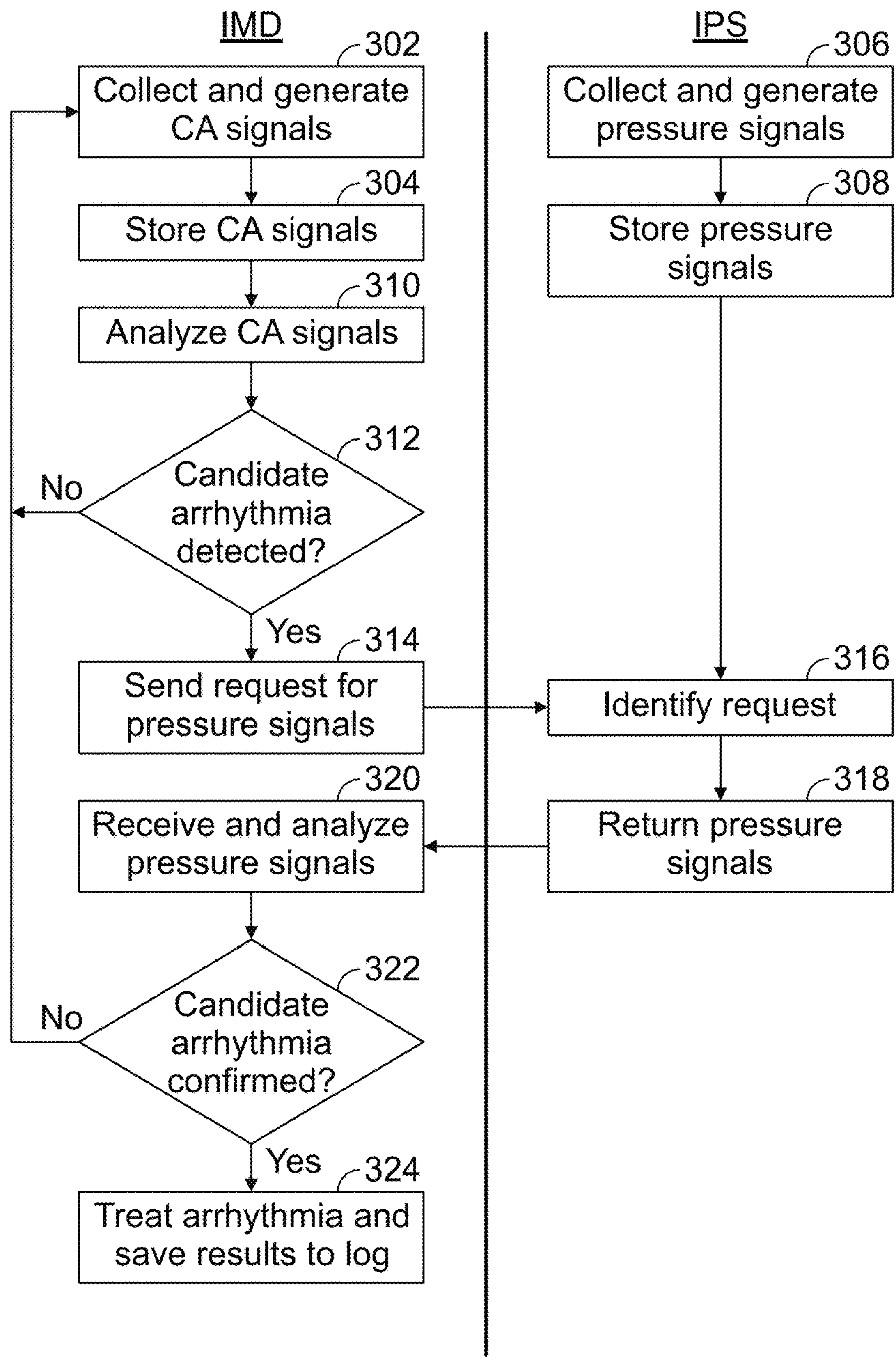
FIG. 3A illustrates a method for detecting and confirming a candidate arrhythmia with the IMD based on cardiac activity (CA) signals associated with the IMD and pressure signals associated with the IPS in accordance with embodiments herein.

Although the FIGS. 3A-3E primarily discuss the detection and verification of VT, it should be understood that the methods and systems apply equally to the detection and verification of VF as well as AF. FIG. 3A illustrates a method for confirming an arrhythmia with the IMD 100 based on CA signals and pressure signals in accordance with embodiments herein. At 302, one or more processors sense (e.g., collect) cardiac activity (CA) and generate CA signals based on the CA, and at 304, one or more processors, such as of the IMD 100, store the CA signals, such as in a memory. In some embodiments, the memory can store the CA signals for a predetermined amount of time, such as 10 seconds, 30 seconds, one minute, two minutes, or more, depending upon the space available and whether the CA signals are determined to be of interest, such as being indicative of an arrhythmia. The IMD 100 can discard older CA signals in favor of storing more recently acquired CA signals.

Simultaneously, on a schedule and/or on-demand, at 306, one or more processors, such as of the IPS 150, sense (e.g., collect) pressure data and generate pressure signals that are based on the pressure data. At 308, one or more processors store the pressure signals in a memory in the IPS 150, such as memory 160 of FIG. 2. As with the IMD 100, the IPS 150 can store pressure signals for a predetermined amount of time, such as 30 seconds, one minute, two minutes, etc. In some embodiments the pressure signals can be stored in a running loop, such that older data is overwritten or otherwise deleted as more pressure signals are collected and stored. In some embodiments, the IPS 150 can collect pressure signals at predefined intervals, substantially in real-time by continuously sensing pressure, and/or on-demand, such as upon receiving a signal or other request to sense pressure, such as for a predetermined amount of time.

At 310, one or more processors associated with the IMD 100 analyze the CA signals to detect a candidate arrhythmia. For example, the IMD ventricular rate (v-rate), the CA-based rate, over one or more cardiac cycles, can be determined. If the CA-based rate is elevated and/or exceeds a threshold, the one or more processors may determine that a candidate arrhythmia is detected. Additionally or alternatively, a candidate arrhythmia may be identified by comparing the CA signals to one or more templates.

At 312, if the one or more processors determine that no candidate arrhythmia is detected, flow can return to 302. If the one or more processors detect a candidate arrhythmia such as VT, the method passes to 314 to start a process of confirming the candidate arrhythmia before administering treatment to the patient. For example, in some cases, the IMD v-rate can be elevated due to oversensing of P or T waves, and thus the mean IMD v-rate will be higher than the actual or true ventricular rate.

Figure 5:
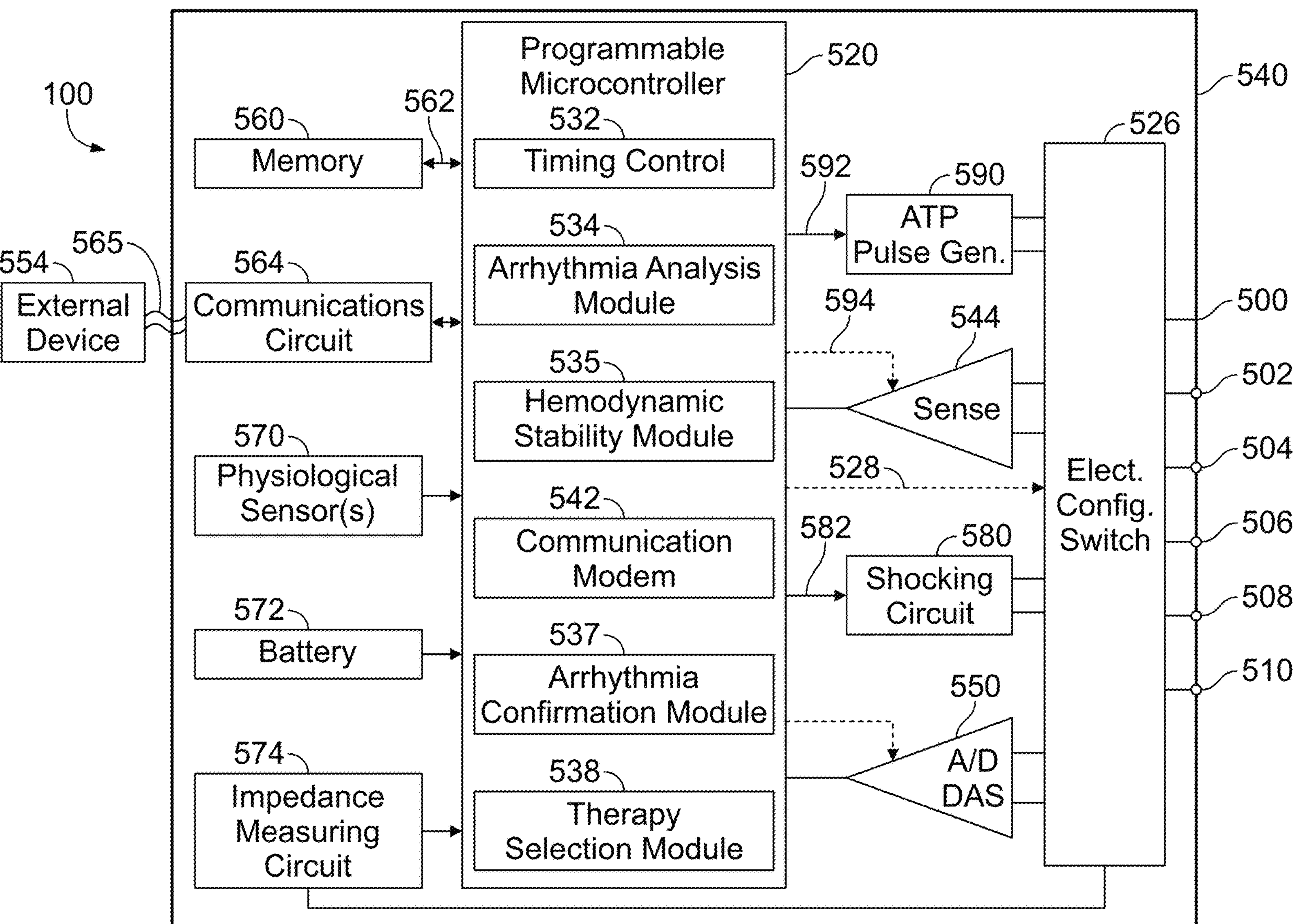
FIG. 5 shows an example block diagram of the IMD formed in accordance with embodiments herein.

At 314, the one or more processors send a request, such as to the IPS 150, for pressure signals. For example, the one or more processors can direct IMD communications circuit 564 and/or communication modem 542 (as shown in FIG. 5) to transmit the request to the IPS communications circuit 158 (FIG. 2). In some embodiments, if the IPS 150 collects pressure signals on a continuous or near-continuous basis, the IMD 100 can send a request for pressure signals that were collected at a defined time or within a particular time period. In other embodiments, if the IPS 150 waits to collect pressure signals until receiving a request from the IMD 100 or other device, the request sent by the IMD 100 can include the request for the IPS 150 to activate the sensing/collection function.

At 316, the one or more processors associated with the IPS 150 identify the request from the IMD 100. If needed, the IPS 150 can activate the sensing/collection function to collect pressure signals (306). If pressure signals for cardiac cycles corresponding to the one or more cardiac cycles are already stored in the memory (308), such as corresponding to a predetermined time period, or after the pressure signals for one or more cardiac cycles are stored in the memory, at 318 the one or more processors can return the pressure signals to the IMD 100. In some cases, the IPS 150 will identify the cardiac cycles corresponding to the request from the IMD 100 (e.g., the same cardiac cycles in time), while in other cases the IPS 150 will transmit all or a portion of the stored pressure signals. The IPS 150 can continue collecting pressure signals in real-time or substantially real-time, and sending the pressure signals to the IMD 100, such as for a predetermined period of time and/or until notified by the IMD 100 or other device to stop collecting and/or transmitting pressure signals.

At 320, the one or more processors associated with the IMD 100 can receive and analyze the pressure signals for the one or more cardiac cycles that correspond to the candidate arrhythmia to confirm or deny the candidate arrhythmia. In some embodiments, one or more cardiac cycles of the CA signals and the pressure signals that correspond in time with each other can be compared to each other. For example, the mean IPS v-rate, the pressure-based rate, over one or more cardiac cycles (e.g., a predetermined length of time and/or time period) can be determined and compared to the mean IMD v-rate, the CA-based rate, over the corresponding time period.

At 322, the one or more processors confirm or deny the candidate arrhythmia based on a comparison of the CA and pressure-based rates. In some embodiments, corresponding cardiac cycles of the CA and pressure-based rates are compared. For example, the IPS v-rate is not susceptible to oversensing of the electrical signal (e.g., EGM). Therefore, if the IPS v-rate and the IMD v-rate are not the same or are not within a predetermined threshold of each other (e.g., the IPS v-rate is lower than the IMD v-rate), the candidate arrhythmia is denied, and flow can return to 302. If the candidate arrhythmia is confirmed based on the comparison of the CA and pressure-based rates, flow passes to 324 where the one or more processors can activate circuitry, components, and/or processes to treat the arrhythmia. Accordingly, the method provides the technical benefit of confirming the candidate arrhythmia prior to treating the patient, and thus the patient is spared unnecessary and/or painful treatment.

Although the candidate arrhythmia analysis of FIG. 3A is discussed with respect to a first example, that is, primarily in terms of comparing the mean IMD v-rate and mean IPS v-rate (e.g., comparison of a CA-based rate and a pressure-based rate over a defined period of time) to confirm the candidate arrhythmia, other verification methods can be used. In a second example, signal features of the pressure signals of the IPS 150 can be compared to stored corresponding signal features of pressure signals collected during normal sinus rhythm (NSR). Referring again to FIG. 3A, at 320 the one or more processors analyze the pressure signals collected and returned by the IPS 150 to identify signal features. Signal features of interest can include, but are not limited to, pulse pressure, systolic pressure, diastolic pressure, duration of systole, maximum pressure slope ($dP/dT_{max}$), area under curve of the pressure signal (AUC), amplitude, markers, and the like. Other features of the sinus template may be used for comparison. If the one or more processors determine that the signal features between the pressure signals associated with the candidate arrhythmia and the signal features of the NSR template are similar, such as based on a correlation coefficient, thresholds, etc., the candidate arrhythmia is denied, while if the comparison is dissimilar, the candidate arrhythmia is confirmed.

In a third example, an overall pressure signal waveform can be compared to a saved template. For example, an NSR template of the pressure signals can be collected and saved when the patient is not experiencing an arrhythmia or other abnormality. Referring to FIG. 3A, at 320, the one or more processors analyze the pressure signals by comparing a representative pressure signal waveform of the returned pressure signals to the NSR template, such as to determine a correlation coefficient. If the returned pressure signals and the NSR template are determined to be sufficiently similar, the candidate arrhythmia is denied. The comparison of the template can be used to determine when the pressure signals indicate a pressure-indicated arrhythmia.

In other cases, feature(s) of the pressure signals of the IPS 150 can be evaluated for the presence of atrial fibrillation (AF). In some cases, the VT detection by the IMD 100 (e.g., the candidate arrhythmia detected at 312 of FIG. 3A) is caused by rapid ventricular rate driven by AF during which IMD therapy intended for the ventricle should be avoided. The pressure signal morphology is expected to vary significantly from beat to beat during AF as the ventricle is subject to significantly varying diastolic intervals. Some beats, however, will have long diastolic interval thus leading to similar morphological features to those observed during NSR. Additionally, hemodynamics will not suffer significantly during AF such that PAP features will exceed (e.g., exceed negatively or positively) to indicate hemodynamic instability compared to thresholds defined for minimum hemodynamics.

Therefore, in a fourth example, in response to the candidate arrhythmia, based on the CA signals, being declared a VT, morphological features of the pressure signals and an NSR template can be compared to determine similarity therebetween. In FIG. 3A, at 320, the one or more processors compare morphological features of at least two beats of the returned pressure signals from the IPS 150 to morphological features of the NSR template. If a certain percentage of beats during VT detection have similar morphological features to those of the NSR template, the patient is likely experiencing AF instead of VT, and the detected candidate arrhythmia is denied, as treatment is not required.

In a fifth example, one or more PAP features can be compared to thresholds defined for hemodynamic instability (e.g., hemodynamic compromise), which is further discussed below in FIGS. 4A-4C. In FIG. 3A, at 320, the one or more processors analyze one or more PAP features of the returned pressure signals to determine if the one or more PAP features are above thresholds defined for hemodynamic instability. If all or a subset of the PA pressure features are above the thresholds, the diagnosis is likely AF and the candidate arrhythmia is denied, as treatment is not required.

Figure 3B:
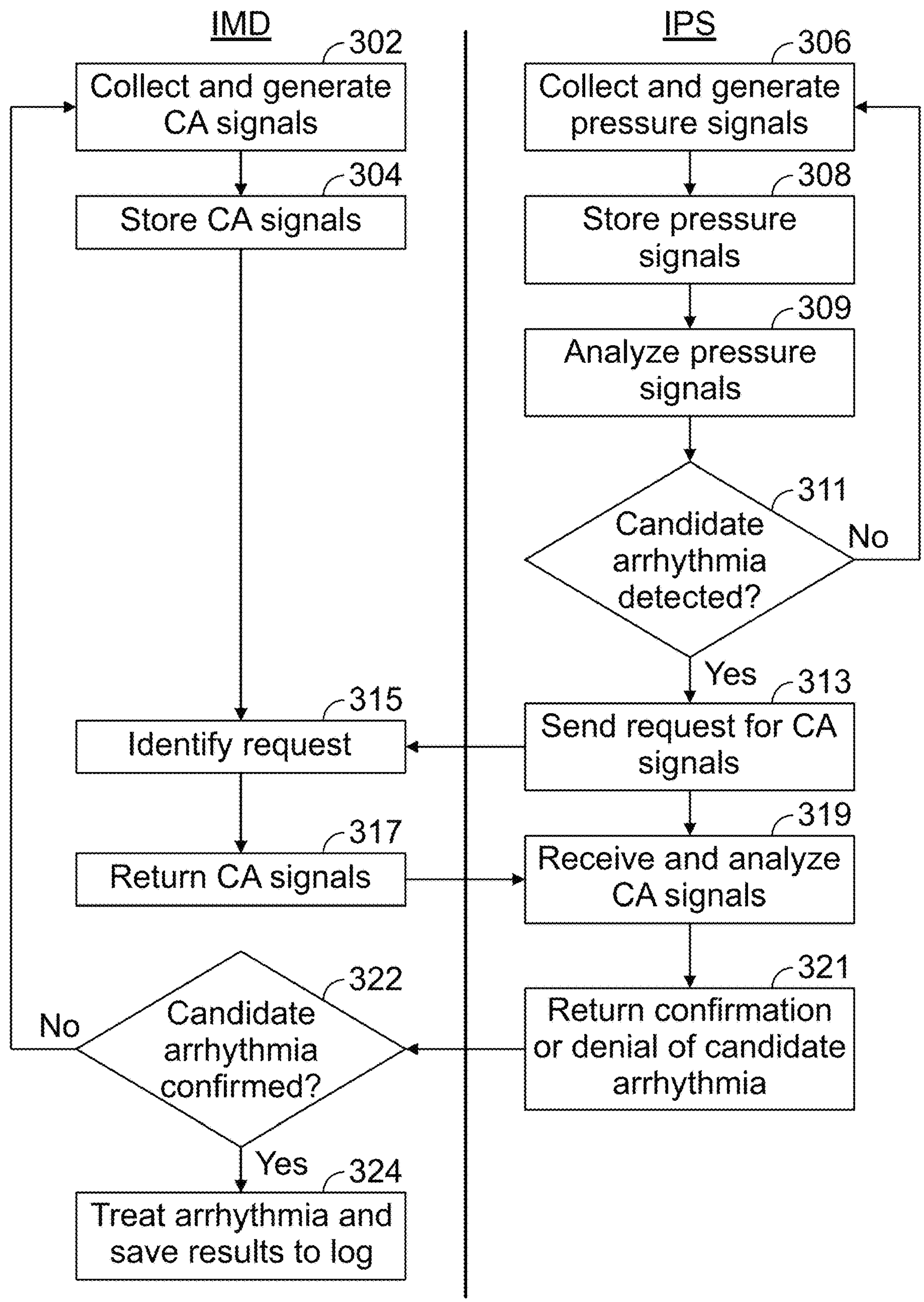
FIG. 3B illustrates a method for detecting and confirming a candidate arrhythmia with the IPS in accordance with embodiments herein.

FIG. 3B illustrates a method for detecting and confirming a candidate arrhythmia with the IPS 150 in accordance with embodiments herein. The collection of CA and generation of CA signals and the collection of pressure data and generation of pressure signals as described in 302, 304, 306, and 308 of FIG. 3A are substantially similar and will not be further discussed. It should be understood that the candidate arrhythmia analysis and confirmation or denial can be accomplished based on one or more of the examples described herein.

At 309, the one or more processors associated with the IPS 150 analyze the pressure signals. For example, the one or more processors associated with the IPS 150 can analyze the pressure signals similar to the analysis discussed above in 320, such as to identify signal features. Signal features of interest can include, but are not limited to, pulse pressure, systolic pressure, diastolic pressure, duration of systole, maximum pressure slope ($dP/dT_{max}$), area under curve of the pressure signal (AUC), amplitude, markers, and the like. At 311, the one or more processors associated with the IPS 150 determine whether a candidate arrhythmia is detected. If no, the flow returns to 306. If yes, at 313 the one or more processors send a request to the IMD 100 for the CA signals. At 315, the one or more processors associated with the IMD 100 identify the request and at 317, return the CA signals to the IPS 150.

At 319, the one or more processors associated with the IPS 150 receive and analyze the CA signals to determine whether the candidate arrhythmia is confirmed or denied. At 321, the one or more processors return the confirmation or denial of the candidate arrhythmia to the IMD 100.

At 322, if the candidate arrhythmia is not confirmed, flow returns to 302. If the candidate arrhythmia is confirmed, at 324, the one or more processors treat the arrhythmia as discussed previously.

Figure 3C:
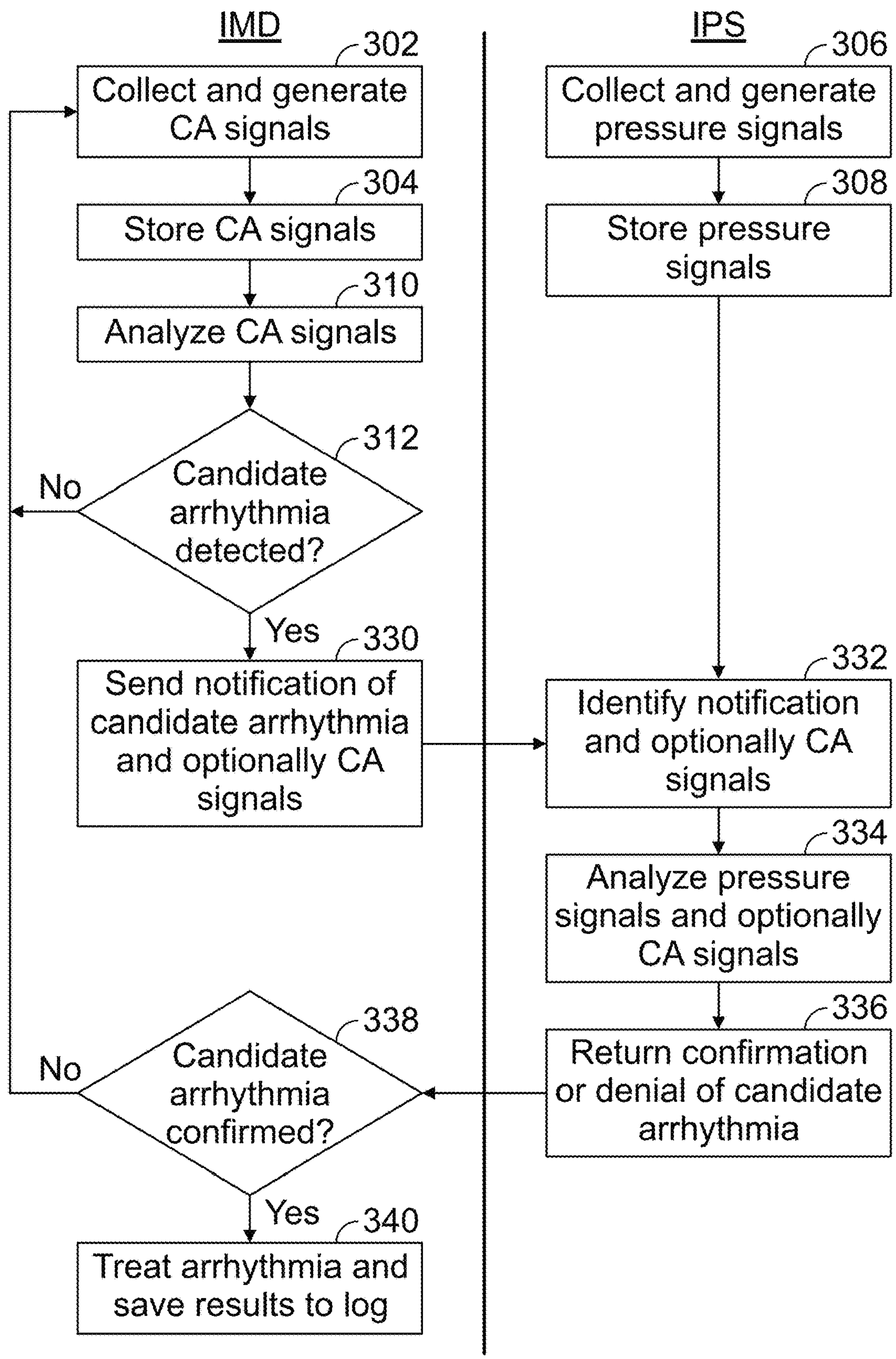
FIG. 3C illustrates a method for confirming a candidate arrhythmia with the IPS based on the CA signals and the pressure signals in accordance with embodiments herein.

FIG. 3C illustrates a method for confirming an arrhythmia with the IPS 150 based on CA signals and pressure signals in accordance with embodiments herein. The collection of CA and generation of CA signals and the collection of pressure data and generation of pressure signals as described in 302, 304, 306, and 308 of FIG. 3A, along with the analysis of the CA signals and the determination of whether a candidate arrhythmia is detected as described in 310 and 312, are substantially similar and will not be further discussed. It should be understood that the candidate arrhythmia analysis can be accomplished based on one or more of any of the examples described herein.

At 312, if the one or more processors determine that no candidate arrhythmia is detected, flow can return to 302. If the one or more processors detect a candidate arrhythmia, the method passes to 330 to send a notification of the candidate arrhythmia to the IPS 150. In some embodiments, if the IPS 150 is going to process any of the CA signal data and/or compare any of the CA signal data to pressure signal data, the one or more processors also transmit/communicate the appropriate CA signals and/or data, such as the one or more cardiac cycles associated with the candidate arrhythmia.

At 332, the one or more processors associated with the IPS 150 receive and identify the notification from the IMD 100, and can optionally receive the CA signals. At 334, the one or more processors associated with the IPS 150 analyze the pressure signals (and optionally the CA signals) to confirm or deny the candidate arrhythmia, such as by using any of the processing/comparing methods disclosed herein and/or known in the art.

At 336, the one or more processors return a confirmation or denial of the candidate arrhythmia to the IMD 100. At 338, the one or more processors determine if the IPS 150 confirmed or denied the candidate arrhythmia in response to the indication received from the IPS 150. If the candidate arrhythmia is confirmed, flow passes to 340 where the one or more processors can activate circuitry, components, and/or processes to treat the arrhythmia. Also, in some embodiments, results can be saved to a log or other file in memory. If the candidate arrhythmia is not confirmed at 338, flow can return to 302.

Detection of VT by Implantable Pressure Sensor

Figure 3D:
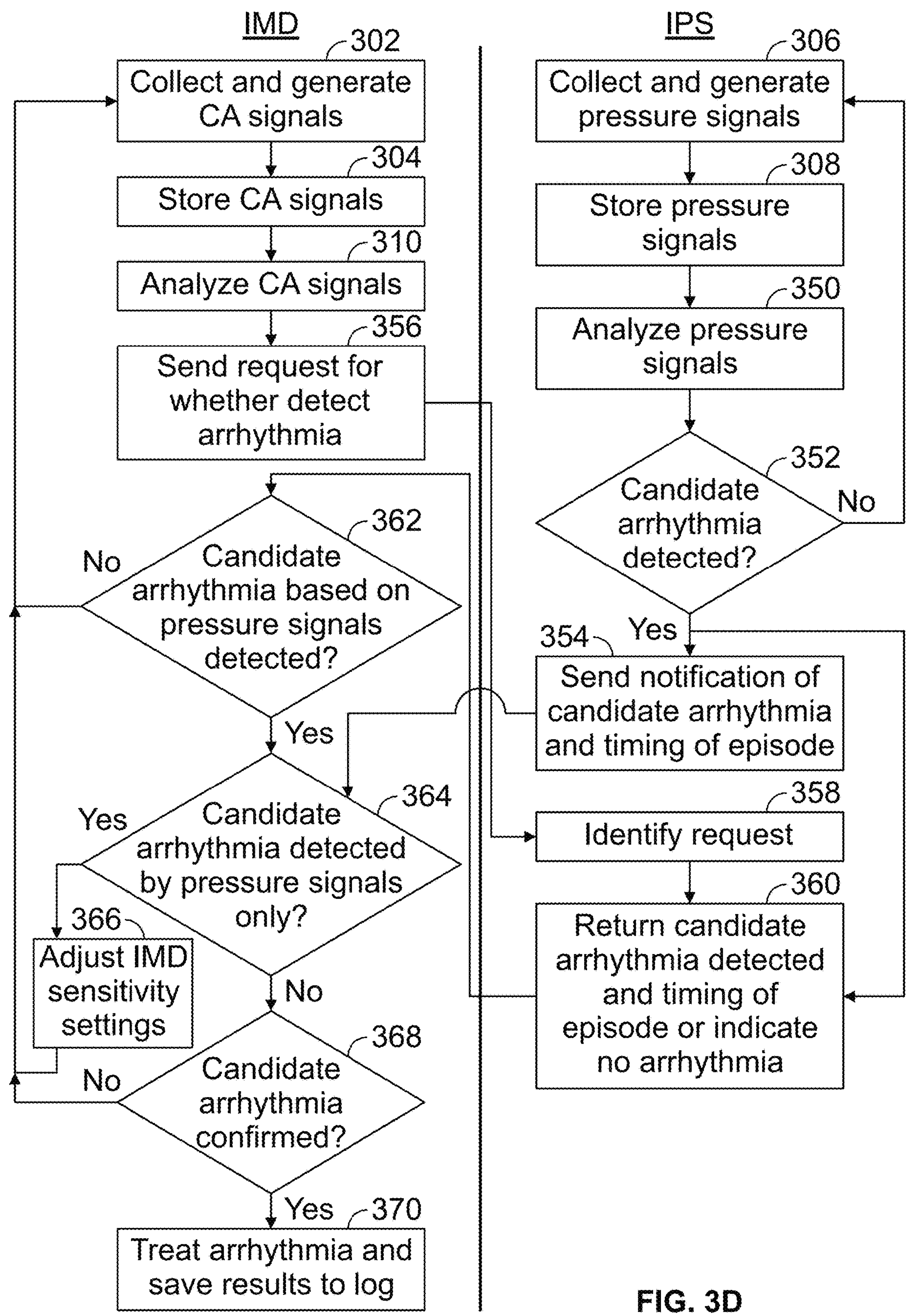
FIG. 3D illustrates a method for adjusting IMD sensitivity settings when the candidate arrhythmia is detected based on the pressure signals and not detected based on the CA signals in accordance with embodiments herein.

FIG. 3D illustrates a method for adjusting IMD sensitivity settings when the candidate arrhythmia is detected based on the pressure signals and not detected based on the CA signals in accordance with embodiments herein. For example, it is possible for the VT (e.g., candidate arrhythmia) to be detected based on the pressure signals of the IPS 150 but not by the IMD 100 due to EGM attenuation during VT.

In FIG. 3D, the pressure signals can by analyzed by the IPS 150 to detect the candidate arrhythmia, or the pressure signals can be sent/transmitted to the IMD 100 in real-time, in response to a request, and/or on a predetermined basis and the IMD 100 can analyze the pressure signals to detect the candidate arrhythmia. The collection of CA and generation of CA signals and the collection of pressure data and generation of pressure signals as described in 302, 304, 306, and 308 of FIG. 3A, and the analysis of the CA signals in 310 are substantially similar and will not be further discussed. It should be understood that the candidate arrhythmia analysis of the CA signals and the pressure signals can be accomplished based on one or more of any of the examples described herein.

Turning first to the IPS 150, at 350 the one or more processors analyze pressure signals collected and returned by the IPS 150 to identify signal features, such as in the second example described above. Namely, signal features of the pressure signals of the IPS 150 can be compared to stored corresponding signal features of pressure signals collected during normal sinus rhythm (NSR). If the one or more processors determine that the signal features between the pressure signals associated with the candidate arrhythmia and the signal features of the NSR are similar, the candidate arrhythmia is denied by the one or more processors at 352 and flow returns to 306. However, if the signal features being compared are different, at 352 the one or more processors confirm the candidate arrhythmia and flow passes to 354 and/or 360 (discussed further below). At 354, the one or more processors send a notification to the IMD 100 that indicates that a candidate arrhythmia has been detected based on the pressure signals, and can also send pressure signals and/or data indicating timing of the candidate arrhythmia episode.

Turning to the IMD 100, at 356, the one or more processors send a request to the IPS 150 to inquire whether the IPS 150 has detected a candidate arrhythmia. The IMD 100 can poll the IPS 150 at regular intervals or based on a trigger, etc. In some embodiments, the sending of the request is not based on whether the IMD 100 has detected a candidate arrhythmia.

At 358, the one or more processors associated with the IPS 150 identify the request, and at 360, the one or more processors receive the confirmation or denial of a candidate arrhythmia associated with the pressure signals, such as from 352, and return an indication that no arrhythmia was detected based on the pressure signals or return a confirmation that a candidate arrhythmia was detected. Optionally, the pressure signal data and/or data indicating timing of the candidate arrhythmia episode can be transmitted.

At 362, the one or more processors associated with the IMD 100 determine whether a candidate arrhythmia was detected based on the pressure signals of the IPS 150. If no, flow can return to 302. Other processes and/or methods may also determine whether the CA signals indicated a candidate arrhythmia as discussed herein. If the candidate arrhythmia based on the pressure signals is detected, at 364 the one or more processors determine whether the candidate arrhythmia was detected based on pressure signals only. For example, the one or more processors previously analyzed the CA signals at 310, and can identify a candidate arrhythmia based on the CA signals using any of the proposed methods herein.

If a candidate arrhythmia was not detected based on the analyzed CA signals at 310, but was detected by the pressure signals, flow passes to 366 and the one or more processors adjust the IMD sensitivity settings. In some embodiments, the IMD 100 can increase the sensitivity of ventricular event detection (e.g., lowering R sense threshold), to confirm the presence of rapid ventricular rate. In some cases, one adjustment (e.g., an aggressive adjustment) can be made, while in other cases the adjustment can be made over two or more iterations. Flow can return to 302, where additional CA signals are acquired and then analyzed to confirm or deny the candidate arrhythmia. In some cases, the adjustment of the sensitivity settings and determination of whether the candidate arrhythmia is confirmed or denied can be repeated.

If at 364 the candidate arrhythmia is detected by both the CA signals and the pressure signals, flow passes to 368 and the one or more processors confirm or deny the candidate arrhythmia. If the candidate arrhythmia is denied, flow can return to 302. If the candidate arrhythmia is confirmed, flow passes the 370 where the one or more processors activate circuitry, components, and/or processes to treat the arrhythmia. Also, in some embodiments results can be saved to a log or other file in memory.

Figure 3E:
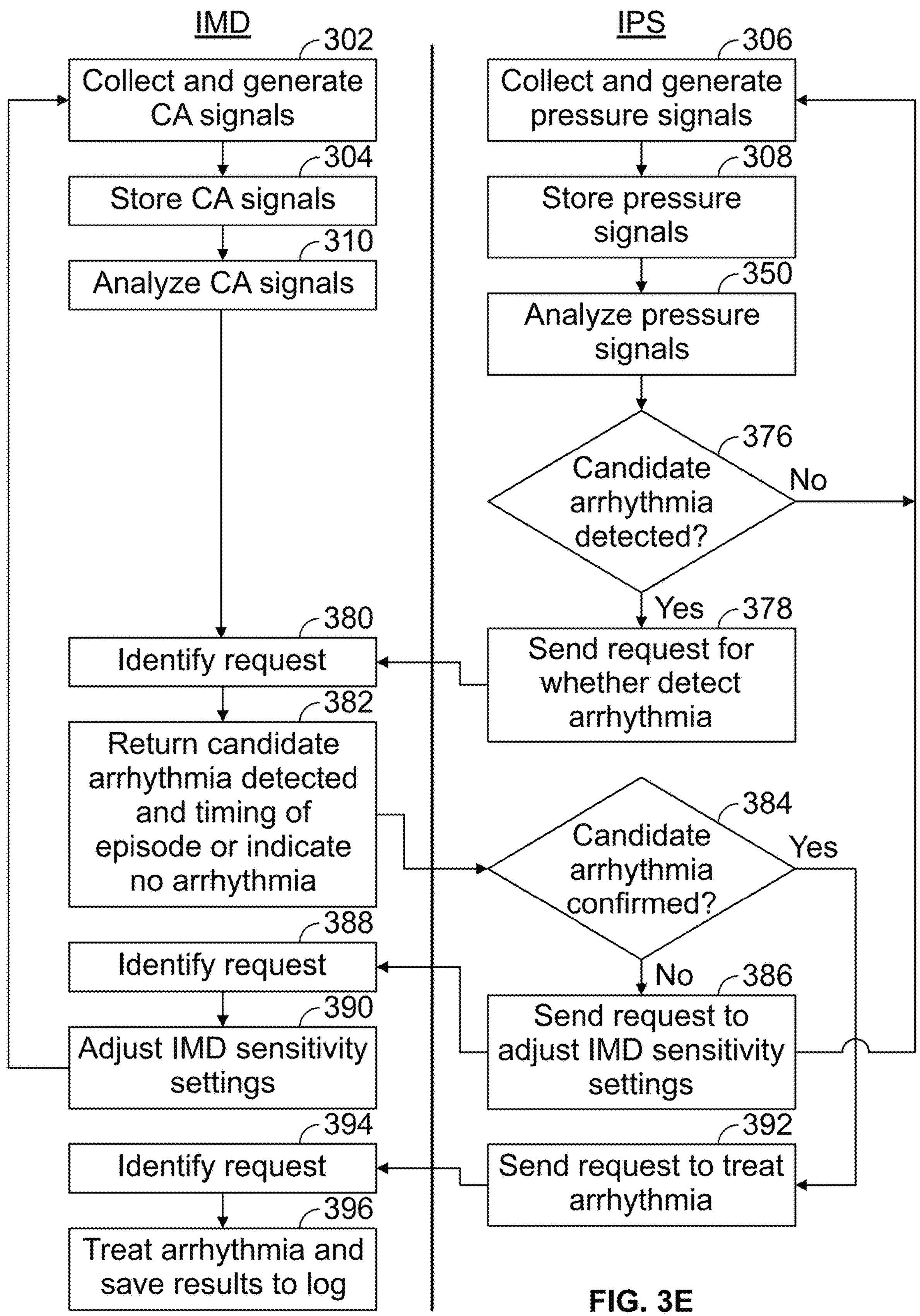
FIG. 3E illustrates a method for confirming, with the IPS, a candidate arrhythmia that is detected based on the pressure signals and not detected based on the CA signals and adjusting IMD sensitivity settings in accordance with embodiments herein.

FIG. 3E illustrates a method for confirming, with the IPS 150, a candidate arrhythmia that is detected based on the pressure signals and not detected based on the CA signals in accordance with embodiments herein. The collection of CA and generation of CA signals and the collection of pressure data and generation of pressure signals as described in 302, 304, 306, and 308 of FIG. 3A, the analysis of the CA signals as described in 310 of FIG. 3A, and the analysis of the pressure signals as described in 350 of FIG. 3D are substantially similar and will not be further discussed. It should be understood that the candidate arrhythmia confirmation can be accomplished based on one or more of any of the examples described herein.

Turning to the IPS 150, at 376, the one or more processors determine whether a candidate arrhythmia is detected in response to the analysis of the pressure signals. If a candidate arrhythmia is not detected, flow can return to 306. If a candidate arrhythmia is detected, at 378, the one or more processors send a request to the IMD 100 to inquire whether the IMD 100 has detected a candidate arrhythmia based on the CA signals.

Turning to the IMD 100, at 380 the one or more processors receive and identify the request. At 382, the one or more processors return an indication that no arrhythmia was detected based on the CA signals (e.g., analysis of CA signals at 310) or return a confirmation that a candidate arrhythmia was detected. Further, the CA signal data and/or data indicating timing of the candidate arrhythmia episode can be transmitted.

At 384, the one or more processors determine whether the candidate arrhythmia detected at 376 is confirmed by the IMD 100. If no, at 386 the one or more processors send a request to the IMD 100 to adjust IMD sensitivity settings and can return to 306.

At 388, the one or more processors of the IMD 100 identify the request and at 390, adjust the IMD sensitivity settings, as discussed previously in 366 of FIG. 3D. Flow passes to 302 to collect the CA signals based on the adjusted sensitivity settings.

Returning to 384, if the candidate arrhythmia is detected by both the CA signals and the pressure signals, the one or more processors confirm the candidate arrhythmia and flow passes to 392. At 392, the one or more processors send a request to the IMD 100 to treat the confirmed arrhythmia.

At 394, the one or more processors of the IMD 100 receive and identify the request, and at 396, the one or more processors activate circuitry, components, and/or processes to treat the arrhythmia. Also, in some embodiments results can be saved to a log or other file in memory.

Differentiation Between Stable and Unstable VT

It is desirable to differentiate between stable VT and unstable VT in order to identify an appropriate therapy to administer to the patient. For example, a stable VT may be treated with a low-voltage level therapy such as ATP or therapy may be withheld during further monitoring. An unstable VT, however, may be treated with medium and/or high-voltage shock therapies and/or combinations of therapies.

Once the VT is confirmed or verified, such as discussed in FIGS. 3A-3E, the IMD 100 and/or IPS 150 can determine whether the VT is stable or unstable. In stable VT, the right ventricular (RV) pulse pressure may not significantly reduce compared to the NSR template, whereas a significant reduction may be detected in unstable VT. In some embodiments, various features of the pressure signals of the IPS 150 (e.g., pulse pressure, systolic pressure, diastolic pressure, $dP/dt_{max}$, etc.) can be monitored leading into VT detection. For example, as pulmonary arterial pressure (PAP) reflects the RV pulse pressure, the PAP remains relatively unchanged going from NSR into stable VT, but becomes much smaller in unstable VT. In other embodiments, the various features of the pressure signals of the IPS 150 can be monitored and evaluated when the candidate arrhythmia is detected based on the CA signals and/or pressure signals.

Figure 4A:
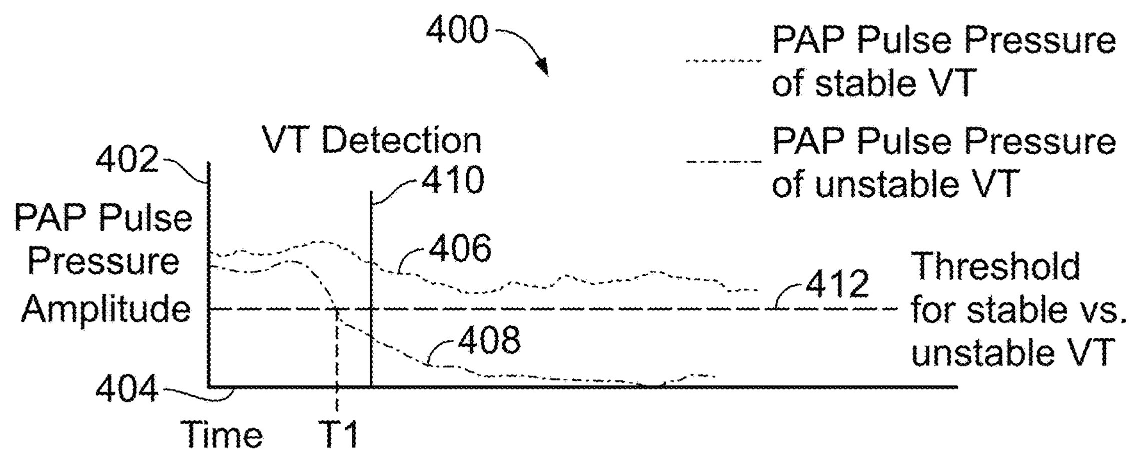
FIG. 4A shows a graph of pulse pressures, associated with stable ventricular tachycardia (VT) and unstable VT, of a pulmonary arterial pressure sensor over time that can be used to differentiate between stable and unstable arrhythmias based on magnitude of one or more pressure signal features in accordance with embodiments herein.

FIG. 4A shows a graph 400 of pulse pressures, associated with stable VT and unstable VT, of a pulmonary arterial pressure sensor over time that can be used to differentiate between stable and unstable arrhythmias based on magnitude of one or more pressure signal features in accordance with embodiments herein. Vertical axis 402 indicates a measure of a magnitude of a pulse portion of the pulse pressure associated with the IPS 150, and horizontal axis 404 indicates time. In some embodiments the magnitude can be an amplitude of the pulse portion of the pulse pressure. Lines associated with stable VT 406 and unstable VT 408 indicate pulse pressures collected over time during a stable VT and an unstable VT, respectively.

For the IPS 150 that is positioned in the pulmonary artery, in some embodiments the IPS 150 measures the pulsatility that is created by the regular contraction of the left ventricle. In VT and some cases of defibrillation, there is no organized contraction, so pulse pressure and thus pulsatility will diminish. In cases of VF, there is no blood flow, so pulsatility quickly drops to zero/near zero.

For a period of time before VT detection 410, the magnitudes of both the stable and unstable VT 406, 408 are above or positively exceed a hemodynamic stability threshold 412. At time T1, the magnitude of the unstable VT 408 goes beyond (e.g., negatively exceeds) or decreases to be below the hemodynamic stability threshold 412, indicating that the pulse pressure may be dropping to an unsafe level. For example, when the VT is unstable, not as much blood is pumped out of the heart compared to during stable VT, thus indicated by the pulse pressure decreasing to below the hemodynamic stability threshold 412. The unstable VT 408 further decreases after the VT detection 410. In contrast, the stable VT 406 degrades over time, indicating that during a stable VT condition the pulse pressure may decrease after the VT detection 410, but remains at a safer level above the hemodynamic stability threshold 412.

Although a single threshold 412 is shown, in some embodiments more than one threshold 412 can be used.

In some embodiments, the pulse pressure can be collected, such as by one or more processors of the IPS 150, and monitored or tracked, such as by one or more processors of the IPS 150 and/or IMD 100, during time periods when an arrhythmia is not occurring. In other embodiments, the pulse pressure can be collected and tracked starting, for example, at the VT detection 410. The magnitudes of the pulse pressures can be compared to the hemodynamic stability threshold 412 over time. In some cases, if the arrhythmia is classified as a stable VT, a less-intensive therapy can be administered, such as ATP. In other cases, if the arrhythmia is classified as an unstable VT, such as when the magnitude of the pulse pressure is below the hemodynamic stability threshold 412, a more-intensive therapy can be administered, such as shock from one or more coils and/or electrodes associated with the IMD 100 (e.g., implantable cardiac defibrillator (ICD) shock) or a combination of ATP and ICD shock, for example. Other therapies and combinations of therapies can be used, and as the pulse pressure is monitored over time, the therapy can be changed. For example, if ATP was administered and the pulse pressure falls below the hemodynamic stability threshold 412, the one or more processors of the IMD 100 can administer a more-intensive therapy, such as by applying a level of ICD shock. Conversely, if the pulse pressure increases over time and the magnitude exceeds (e.g., positively exceeds) or increases to be above the hemodynamic stability threshold 412, the one or more processors of the IMD 100 can administer a less-intensive therapy or withhold therapy.

Figure 4B:
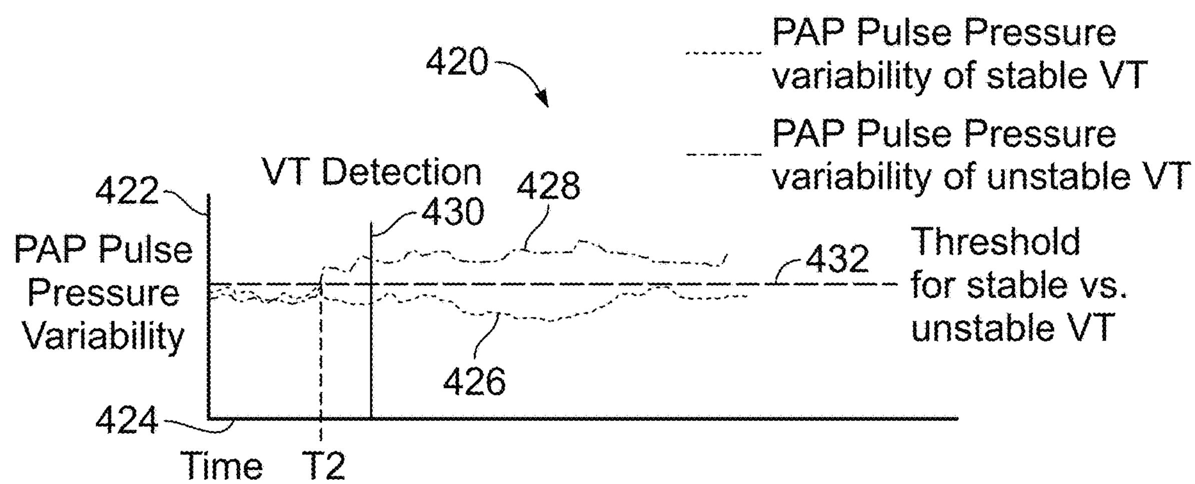
FIG. 4B shows a graph of variability of absolute pulse pressures, associated with stable VT and unstable VT, over time, of a pulmonary arterial pressure sensor in accordance with embodiments herein.

FIG. 4B shows a graph 420 of variability of absolute pulse pressures, associated with stable VT and unstable VT, over time, of a pulmonary arterial pressure sensor in accordance with embodiments herein. Vertical axis 422 indicates an absolute value of a measure of the pulse portion of the pulse pressure associated with the IPS 150, and horizontal axis 424 indicates time. Lines associated with stable VT 426 and unstable VT 428 indicate variabilities of pulse pressures collected over time during a stable VT and an unstable VT, respectively. As shown in the graph 420, the amount of PAP pulse pressure variability detected during the unstable VT 428 increases before VT detection 430 (exceeding hemodynamic stability threshold 432 at T2) and continues to experience a greater level of variability compared to the stable VT 426.

In stable VT, various PAP features may remain stable as the arrhythmia is not hemodynamically compromised, whereas in unstable VT, the features may vary from beat to beat, especially if the unstable VT is polymorphic in nature (e.g., the QRS complex varies compared to the primarily single morphology of the QRS complex of a monomorphic VT). In addition, the electromechanical coupling interval (EMCI), measured from IMD v-sense (e.g., v-sense sensed by the IMD 100) to PAP v-sense (e.g., v-sense sensed by the IPS 150), may be used for variability evaluation. As shown, EMCI variability is lower in stable VT and higher in unstable VT. Therefore, by tracking the variability of various PAP and PAP/EGM features, stable vs. unstable VT differentiation can be accomplished.

Figure 4C:
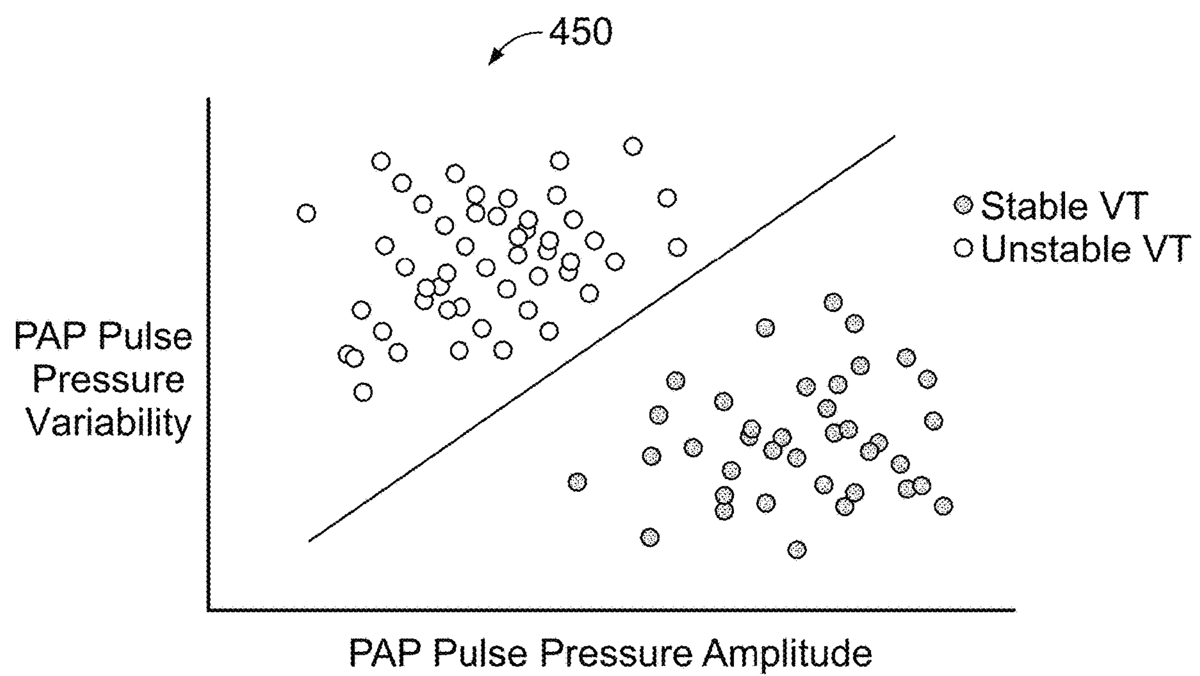
FIG. 4C shows a plot of pulse pressure variability and pulse pressure amplitude combined to differentiate stable vs. unstable arrhythmia in accordance with embodiments herein.

FIG. 4C shows a plot 450 of PAP pulse pressure variability (as discussed in FIG. 4B) and PAP pulse pressure amplitude (as discussed in FIG. 4A) combined to differentiate stable vs. unstable VT in accordance with embodiments herein. The PAP pulse pressure amplitude and PAP pulse pressure variability for each heart beat over a period of time is plotted. As can be seen in the plot 450, relatively higher PAP pulse pressure variability combined with relatively lower PAP pulse pressure amplitude can indicate unstable VT. In some cases, the combination of amplitude and amplitude variability may lead to better differentiation than each metric alone.

In some embodiments, communication between the IMD 100 and IPS 150 can provide a technical advantage by identifying electromechanical dissociation, which results in pulseless electrical activity (PEA). In some cases, the IMD 100 may interpret the resulting ECG as normal pulse or normal rhythm. When PEA is occurring, the IPS 150 indicates no pulsative activity. Therefore, in some cases, such as after the IMD 100 has administered treatment and the ECG appears to have returned to normal, the IPS 150 may continue to acquire pressure signals to confirm that there is pulsatility in the presence of electrical activity. In some embodiments, the IPS 150 may acquire and analyze the pressure signals for a period of time such as approximately five minutes or longer to confirm that PEA is not occurring.

In some cases, the diagnosis of the IMD 100 can be compromised due to sensing issues such as noise detection, pause/brady detection due to undersensing, lead abrasion/fracture, and the like. The IMD 100 diagnosis can be verified by monitoring the presence/absence of ventricular contraction detected by the PAP signal (e.g., the pressure signals detected by the IPS 150). For example, if the IMD 100 detects pause, the PAP waveform evaluation can be triggered, such as by sending a request to the IPS 150, to determine whether the ventricular contraction is present or absent. If ventricular contraction is detected, the original diagnosis of pause detection can be rejected.

Further, although PAP pulse pressure was used as an example PAP signal feature in at least some of the FIGS. 4A-4C, other features for VT verification and stable vs. unstable VT discriminations may include systolic pressure, diastolic pressure, mean pressure, $dP/dT_{max}$, stroke volume, and/or duration of systole or diastole (as percentage of cycle length).

FIG. 5 shows an example block diagram of the IMD 100 formed in accordance with embodiments herein. The IMD 100 may treat both fast and slow arrhythmias, including VA (e.g., further including VF/VT, etc.), with stimulation therapy, including cardioversion, pacing stimulation, suspend tachycardia detection, tachyarrhythmia therapy, and/or the like. In some embodiments, the IMD 100 can be one of an implantable cardioverter defibrillator, pacemaker, cardiac rhythm management device, defibrillator, or leadless pacemaker but is not so limited.

The IMD 100 has a housing 540 to hold the electronic/computing components. The housing 540 (which is often referred to as the "can," "case," "encasing," or "case electrode") may be programmably selected to act as an electrode for certain sensing modes. Housing 540 further includes a connector (not shown) with at least one terminal 500 and optionally additional terminals 502, 504, 506, 508, 510. The terminals 500, 502, 504, 506, 508, 510 may be coupled to sensing electrodes that are provided upon or immediately adjacent the housing 540. Optionally, more or less than six terminals 500, 502, 504, 506, 508, 510 may be provided in order to support more or less than six sensing electrodes. Additionally or alternatively, the terminals 500, 502, 504, 506, 508, 510 may be connected to one or more leads having one or more electrodes provided thereon, where the electrodes are located in various locations about the heart. The type and location of each electrode may vary. The lead can be positioned in one of a transvenous, subcutaneous, or subxiphoid position. In some embodiments, the IMD 100 can be a subcutaneous IMD coupled to an extravascular lead having a first electrode disposed along a distal segment of the lead and a second electrode disposed along a proximal segment of the lead.

The IMD 100 includes a programmable microcontroller 520 that controls various operations of the system 101, including cardiac monitoring. Microcontroller 520 includes a microprocessor (or equivalent control circuitry, one or more processors, etc.), RAM and/or ROM memory, logic and timing circuitry 532, state machine circuitry, and I/O circuitry. The timing circuitry 532 can control the timing of the stimulation pulses (e.g., pacing rate, atrio-ventricular (AV) delay, atrial interconduction (A-A) delay, or ventricular interconduction (V-V) delay, etc.). Microcontroller 520 includes an arrhythmia analysis module 534 that is configured to analyze the cardiac activity (CA) signals over one or more cardiac beats to identify the existence of a candidate arrhythmia. The microcontroller 520 and/or arrhythmia analysis module 534 can declare a candidate arrhythmia episode (e.g., VT or VF arrhythmia) based on the CA signals.

In some embodiments, the arrhythmia analysis module 534 can include morphology detection to review and analyze one or more features of the morphology of cardiac signals. In other embodiments, the arrhythmia analysis module 534 can compare CA signals and/or pressure signals to one or more templates (e.g., stored in memory 560) associated with normal sinus rhythm. The arrhythmia analysis module 534 can analyze the cardiac signals indicative of cardiac events that are sensed by electrodes located proximate to one or more atrial and/or ventricular sites. The cardiac events are sensed over a period of time that includes a detection period that can be followed by an observation period. The cardiac events can be analyzed in accordance with conventional ventricular arrhythmia algorithms, such as conventional tachycardia detection algorithms and/or fibrillation detection algorithms. Based on the analysis, the arrhythmia analysis module 534 can declare a candidate arrhythmia episode, such as SVT block, a ventricular tachycardia episode (TA) or a ventricular fibrillation episode, etc. In some embodiments, the arrhythmia analysis module 534 or other processor(s) of the microcontroller 520 can detect a pause in response to analyzing the CA signals. In response to detecting a pause, the module 534 can analyze the pressure signals to determine whether ventricular contraction is present or absent, and in response to the ventricular contraction being present, reject a diagnosis of pause.

The microcontroller 520 also includes an arrhythmia confirmation module 537 that confirms or denies that a candidate arrhythmia detected by one or both of the IMD 100 and IPS 150 is an arrhythmia that should be treated and/or monitored. For example, the arrhythmia confirmation module 537 can obtain pressure signals for cardiac cycles corresponding to the one or more cardiac cycles of the candidate arrhythmia. In other embodiments, the arrhythmia confirmation module 537, in response to confirming the candidate arrhythmia based on the CA signals and denying the candidate arrhythmia based on the pressure signals, can increase at least one sensitivity setting associated with sensing the cardiac activity. In an additional embodiment, the arrhythmia confirmation module 537 can analyze additional CA signals that are sensed by the IMD sensing circuit and are based on the increased at least one sensitivity setting, and the candidate arrhythmia can be confirmed or denied based on the analysis of the additional CA signals.

Also, the microcontroller 520 further controls a shocking circuit 580 by way of a control signal 582. The shocking circuit 580 generates shocking pulses that are applied to the heart of the patient to terminate the detected arrhythmia through various configurations such as less than a full shock strength of one or more electrode through full shock strength with two or more electrodes, etc. The shocking circuit 580 can generate high-voltage and/or medium-voltage and the shocking electrodes, such as the electrodes as discussed in FIG. 1, can be configured to deliver high-voltage or medium-voltage shocks.

The IMD 100 further includes a first chamber pulse generator 590 that generates stimulation pulses (e.g., ATP) for delivery by one or more electrodes coupled thereto. The pulse generator 590 is controlled by the microcontroller 520 via control signal 592. The pulse generator 590 is coupled to the select electrode(s) via the electrode configuration switch 526, which includes multiple switches for connecting the desired electrodes to the appropriate I/O circuits, thereby facilitating electrode programmability.

In some embodiments, the output of a sensing circuit 544 is connected to the microcontroller 520 which, in turn, triggers or inhibits the pulse generator 590, shocking circuit 580, and/or therapy selection module 538 in response to the absence or presence of cardiac activity, in conjunction with the arrhythmia analysis module 534 and the arrhythmia confirmation module 537. The sensing circuit 544 receives a control signal 594 from the microcontroller 520 for purposes of controlling the gain, threshold, polarization charge removal circuitry (not shown), and the timing of any blocking circuitry (not shown) coupled to the inputs of the sensing circuitry.

The microcontroller 520 also includes a therapy selection module 538 for selecting therapies, such as to address VT and/or VF, from within the collection of therapies stored in the memory 560. In response to determining that the arrhythmia has resolved, or if the patient requires a different (e.g., greater, lesser, or none) shocking therapy, the therapy selection module 538 can change the applied therapy to take the patient's current condition into account.

Further, a hemodynamic stability module 535 can determine whether the pulse pressure signals discussed in FIGS. 4A-4C, if received from the IPS 150, indicate that the candidate arrhythmia is a hemodynamically stable VT or an hemodynamically unstable VT. For example, the hemodynamic stability module 535 can compare amplitudes of pulse pressure over one or more heart beats to a threshold, and/or compare pulse pressure variability to a threshold. If the amplitude decreases below the hemodynamic stability threshold 412 (e.g., amplitude-based threshold) or if the variability increases to be above the hemodynamic stability threshold 432 (e.g., variability-based threshold), the therapy selection module 538 can select a therapy to treat an unstable VT. If the amplitude and/or variability of the pressure signals indicates a stable VT with respect to the applicable threshold, the therapy selection module 538 can select a therapy to treat a stable VT.

The IMD 100 may include one or more physiological sensor 570. For example, sensor 570 may adjust pacing stimulation rate according to the exercise state of the patient, detect changes in cardiac output, changes in the physiological condition of the heart, or diurnal changes in activity (e.g., detecting sleep and wake states). In other cases, the sensor 570 can obtain accelerometer data with respect to a global coordinate system that is defined relative to a gravitational direction that may be utilized to identify a posture of the patient, movement of the IMD 100 within the patient, etc.

While shown as being included within the housing 540, the physiological sensor 570 may be external to the housing 540, yet still, be implanted within or carried by the patient.

Although not shown, the microcontroller 520 may further include other dedicated circuitry and/or firmware/software components that assist in monitoring various conditions of the patient's heart and managing pacing therapies.

A switch 526 is optionally provided to allow selection of different electrode configurations under the control of the microcontroller 520. The electrode configuration switch 526 may include multiple switches for connecting the desired electrodes to the appropriate I/O circuits, thereby facilitating electrode programmability. The switch 526 is controlled by a control signal 528 from the microcontroller 520. Optionally, the switch 526 may be omitted and the I/O circuits directly connected to a housing electrode via terminal 500 and one or more other electrodes via terminals 502, 504, 506, 508, 510.

The IMD 100 is further equipped with a communication modem (modulator/demodulator) 542 to enable wireless communication with other devices, implanted devices such as the IPS 150, and/or external devices 554. In one implementation, the communication modem 542 uses high frequency modulation, for example using RF, Bluetooth or Bluetooth Low Energy telemetry protocols. The signals are transmitted in a high frequency range and will travel through the body tissue in fluids without stimulating the heart or being felt by the patient. The communication modem 542 may be implemented in hardware as part of the microcontroller 520, or as software/firmware instructions programmed into and executed by the microcontroller 520. Alternatively, the modem 542 may reside separately from the microcontroller as a standalone component. The modem 542 facilitates data retrieval from a remote monitoring network. The modem 542 enables timely and accurate data transfer directly from the patient to an electronic device utilized by a physician.

The IMD 100 includes the sensing circuit 544 selectively coupled to one or more electrodes that perform sensing operations, through the switch 526, to sense cardiac activity data/signals indicative of cardiac activity. The sensing circuit 544 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the features of interest. In one embodiment, switch 526 may be used to determine the sensing polarity of the cardiac signal by selectively closing the appropriate switches. The sensing circuit 544 is configured to sense CA, on-demand and in real-time, for one or more cardiac cycles and generate one or more CA signals based on the CA.

In the example of FIG. 5, a single sensing circuit 544 is illustrated. Optionally, the IMD 100 may include multiple sensing circuits, similar to sensing circuit 544, where each sensing circuit is coupled to two or more electrodes and controlled by the microcontroller 520 to sense electrical activity detected at the corresponding two or more electrodes. The sensing circuit 544 may operate in a unipolar sensing configuration or a bipolar sensing configuration. Optionally, the sensing circuit 544 may be removed entirely, and the microcontroller 520 perform the operations described herein based upon the CA signals from the A/D data acquisition system 550 directly coupled to the electrodes. The output of the sensing circuit 544 is connected to the microcontroller 520 which, in turn, determines when to store the cardiac activity data of CA signals (digitized by the A/D data acquisition system 550) in a memory 560.

In some embodiments, the A/D data acquisition system 550 is coupled to one or more electrodes via the switch 526 to sample cardiac activity signals across any pair of desired electrodes.

A communications circuit 564 can be utilized by the IMD 100 to send and receive communications and/or data between the IMD 100 and the external device 554 through communications link 565 and can utilize wireless communication protocols similar to/same as the communication modem 542.

By way of example, the external device 554 may represent a bedside monitor installed in a patient's home and utilized to communicate with the IMD 100 while the patient is at home, in bed or asleep. The external device 554 may be a programmer used in the clinic to interrogate the IMD 100, retrieve data and program detection criteria and other features. The external device 554 may be a handheld device (e.g., smartphone, tablet device, laptop computer, smartwatch and the like) that may be coupled over a network (e.g., the Internet) to a remote monitoring service, medical network and the like. The external device 554 can also act as a one-way and/or bidirectional bridge/gateway to convey messages, requests, and/or signals (e.g., CA signals, pressure signals, etc.) between the IMD 100 and the IPS 150. For example, the external device 554 can receive the pressure signals, requests, and/or other information/messages from the IPS communications circuit 158 and transmit the pressure signals, requests, and/or other information/messages to the IMD communications circuit 564 or communication modem 542, while in other examples the external device 554 can receive the CA signals, requests, and/or other information/messages from the IMD communications circuit 564 or communication modem 542 and transmit the CA signals, requests, and/or other information/messages to the IPS communications circuit 158. The external device 554 may communicate with the communications circuit 564 of the IMD 100 through the communication link 565. The external device 554 facilitates access by physicians to patient data as well as permitting the physician to review real-time CA signals and/or pressure signals as collected by the IMD 100 and/or IPS 150.

The microcontroller 520 is coupled to a memory 560 by a suitable data/address bus 562. The memory 560 stores a collection of arrhythmia therapies. The memory 560 stores the CA signals and can also store pressure signals, templates, as well as markers and other data content associated with detection and determination of the candidate arrhythmia. The memory 560 also stores program instructions for accomplishing the embodiments described herein.

The microcontroller 520 can implement a computer implemented method for detecting an arrhythmia that comprises sensing cardiac activity (CA), for one or more cardiac cycles, at a sensing circuit within an implantable medical device (IMD). One or more CA signals are generated based on the CA. Pressure is sensed, during the one or more cardiac cycles, at an implantable pressure sensor (IPS). A pressure signal is generated based on the pressure. Under control of one or more processors of the microcontroller 520, configured with executable instructions, one of the CA or pressure signals, for the one or more cardiac cycles, are analyzed to detect a candidate arrhythmia, another one of the CA or pressure signals are obtained for cardiac cycles corresponding to the one or more cardiac cycles, and the candidate arrhythmia is confirmed or denied based on the other one of the CA or pressure signals A battery 572 provides operating power to all of the components in the IMD 100. The battery 572 is capable of operating at low current drains for long periods of time. The battery 572 also desirably has a predictable discharge characteristic so that elective replacement time may be detected. As one example, the housing 540 employs lithium/silver vanadium oxide batteries. The battery 572 may afford various periods of longevity (e.g., three years or more of device monitoring). In alternate embodiments, the battery 572 could be rechargeable. See, for example, U.S. Pat. No. 7,294,108, titled "Cardiac event micro-recorder and method for implanting same", which is hereby incorporated by reference.

The IMD 100 further includes an impedance measuring circuit 574, which can be used for many things, including: lead impedance surveillance for proper lead positioning or dislodgement; detecting operable electrodes and automatically switching to an operable pair if dislodgement occurs; measuring thoracic impedance for determining shock thresholds; detecting when the device has been implanted; measuring stroke volume; and detecting the opening of heart valves; and so forth. The impedance measuring circuit 574 is coupled to the switch 526 so that any desired electrode may be used.

Figure 6:
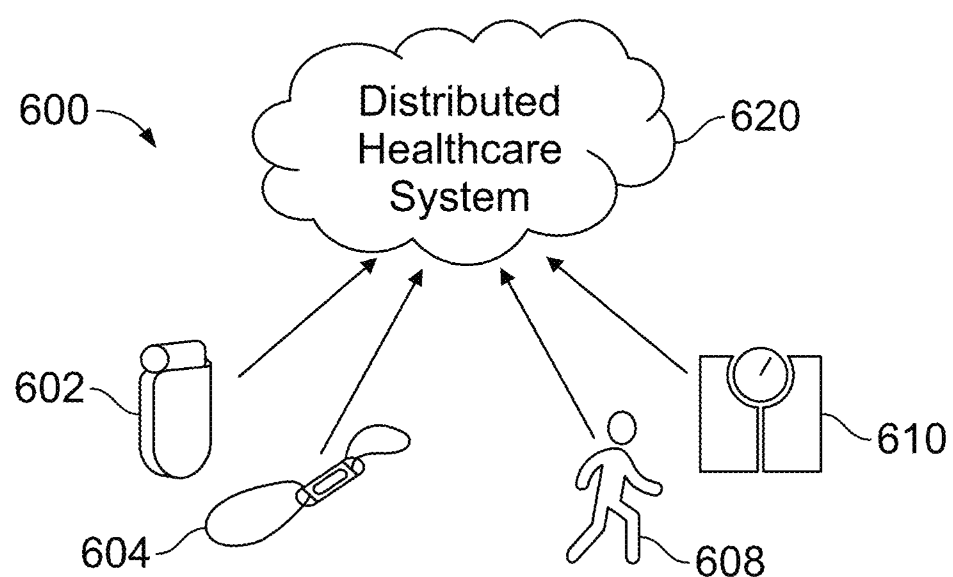
FIG. 6 illustrates a digital healthcare system implemented in accordance with embodiments herein.

FIG. 6 illustrates a digital healthcare system 600 implemented in accordance with embodiments herein. The system 600 utilizes signals detected by an IMD and an IPS, implanted for example in a patient's pulmonary artery, to analyze and confirm candidate arrhythmias. The healthcare system 600 may include wearable devices that communicate with an IMD, IPS, and/or a remote database. As a result, the healthcare system 600 may monitor health parameters of a patient, including arrhythmia episodes (e.g., VA, VT, AF, etc.), applied arrhythmia therapies, etc., and provide a diagnosis for the patient based on the monitored health parameters.

The system 600 may be implemented with various architectures, that are collectively referred to as a healthcare system 620. By way of example, the healthcare system 620 may be implemented as described herein. The healthcare system 620 is configured to receive data, including IMD data, from a variety of external and implantable sources including, but not limited to, active IMDs 602 capable of delivering therapy to a patient, passive IMDs or sensors 604 (e.g., IPS), wearable sensors 608, and point-of-care (POC) devices 610 (e.g., at home or at a medical facility). Any of the IMD 602, sensor 604, sensor 608, and/or POC device 610 may analyze candidate arrhythmias and/or confirm candidate arrhythmias as described herein. The data from one or more of the external and/or implantable sources is collected and communicated to one or more secure databases within the healthcare system 620. Optionally, the patient and/or other users may utilize a device, such as a smart phone, tablet device, etc., to enter data.

Closing

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable media may be utilized. The non-signal media may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. The program instructions may be provided to a processor of a general-purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc., are used merely as labels, and are not intended to impose numerical requirements on their objects or order of execution on their acts.

What is claimed is:

1. A system for arrhythmia detection and confirmation, comprising:

an implantable pressure sensor (IPS);

an implantable medical device (IMD) comprising:

an IMD sensing circuit configured to sense cardiac activity (CA), on-demand and in real-time, for one or more cardiac cycles and to generate one or more CA signals based on the CA;

an IMD communications circuit configured to communicate with at least one of the IPS or an external device;

wherein the IPS comprises:

an IPS sensing circuit configured to sense pressure, on-demand and in real-time, during the one or more cardiac cycles and to generate one or more pressure signals based on the pressure; and an IPS communications circuit configured to communicate with at least one of the IMD or the external device;

wherein at least one of the IMD or IPS further comprises:

memory configured to store program instructions; and one or more processors that, when executing the program instructions, are configured to:

analyze one of the CA or pressure signals, for the one or more cardiac cycles, to detect a candidate arrhythmia;

in response to the detection of the candidate arrhythmia, obtain an other one of the CA or pressure signals for cardiac cycles corresponding to the one or more cardiac cycles; and confirm or deny the candidate arrhythmia based on the other one of the CA or pressure signals.

2. The system of claim 1, wherein the one or more processors and memory are housed in the IMD, the one or more processors configured to:

direct the IMD communications circuit to transmit, to at least one of the IPS communications circuit or the external device, a request for the pressure signals;

receive the pressure signals from at least one of the IPS communications circuit or the external device; and analyze the pressure signals, for the one or more cardiac cycles, to confirm or deny the candidate arrhythmia.

3. The system of claim 1, wherein the one or more processors and memory are housed in the IPS, the one or more processors configured to:

direct the IPS communications circuit to transmit, to at least one of the IMD communications circuit or the external device, a request for the CA signals;

receive the CA signals from at least one of the IMD communications circuit or the external device; and analyze the CA signals, for the one or more cardiac cycles, to confirm or deny the candidate arrhythmia.

4. The system of claim 1, the one or more processors further configured to:

analyze both of the CA and pressure signals to determine a CA-based rate and to determine a pressure-based rate; and confirm or deny the candidate arrhythmia based on a comparison of the CA and pressure-based rates.

5. The system of claim 1, the one or more processors further configured to:

compare the pressure signals, for the one or more cardiac cycles, relative to a template for a normal sinus rhythm to determine when the pressure signals indicate a pressure-indicated arrhythmia; and confirm or deny the candidate arrhythmia based on the comparison of the pressure signals.

6. The system of claim 1, wherein the one or more processors is further configured to:

analyze the CA signals to identify the candidate arrhythmia to be a ventricular tachycardia;

compare the pressure signals, for the one or more cardiac cycles, relative to a template for a normal sinus rhythm to determine when the pressure signals have morphological features that correspond to the normal sinus rhythm; and determine the candidate arrhythmia to be an atrial fibrillation and not the ventricular tachycardia initially identified based on the CA signals based on the comparison of the pressure signals.

7. The system of claim 1, wherein the one or more processors is further configured to:

determine when one or more features of the pressure signals positively or negatively exceed at least one corresponding threshold associated with hemodynamic instability; and identify the candidate arrhythmia to be an atrial fibrillation when all or a subset of the one or more features of the pressure signals positively or negatively exceed the one or more corresponding threshold.

8. The system of claim 1, wherein in response to confirming the candidate arrhythmia based on the CA signals and denying the candidate arrhythmia based on the pressure signals, the one or more processors is further configured to increase at least one sensitivity setting associated with sensing the cardiac activity.

9. The system of claim 8, wherein the one or more processors is further configured to:

analyze additional CA signals that are sensed by the IMD sensing circuit, the additional CA signals based on the increased at least one sensitivity setting; and confirm or deny the candidate arrhythmia based on the analysis of the additional CA signals.

10. The system of claim 1, wherein in response to the one or more processors confirming the candidate arrhythmia associated with the pressure signals, the one or more processors is further configured to:

identify the candidate arrhythmia as a stable arrhythmia if a magnitude of one or more features of the pressure signals is greater than a hemodynamic threshold; and identify the candidate arrhythmia as an unstable arrhythmia if the magnitude of the one or more features of the pressure signals is less than the hemodynamic threshold.

11. The system of claim 10, wherein the one or more features of the pressure signals include at least one of i) pulse pressure, ii) systolic pressure, iii) diastolic pressure, or iv) $dP/dt_{max}$.

12. The system of claim 1, wherein in response to the one or more processors confirming the candidate arrhythmia associated with the pressure signals, the one or more processors is further configured to:

identify the candidate arrhythmia as a stable arrhythmia if a variability of one or more features of the pressure signals is greater than a hemodynamic threshold; and identify the candidate arrhythmia as an unstable arrhythmia if the variability of the one or more features of the pressure signals is less than the hemodynamic threshold.

13. The system of claim 1, wherein the one or more processors is further configured to:

detect a pause in response to analyzing the CA signals;

in response to detecting a pause, analyze the pressure signals to determine whether ventricular contraction is present or absent; and in response to the ventricular contraction being present, reject a diagnosis of pause.

14. The system of claim 1, wherein in response to the confirmation of the candidate arrhythmia, the one or more processors is further configured to treat the candidate arrhythmia.

15. The system of claim 14, wherein the treatment of the candidate arrhythmia includes delivery of i) ATP, ii) a low voltage shock, iii) a medium voltage shock, or iv) a high voltage shock.

16. A computer implemented method for detecting an arrhythmia, comprising:

sensing cardiac activity (CA), for one or more cardiac cycles, at a sensing circuit within an implantable medical device (IMD);

generating one or more CA signals based on the CA;

sensing pressure, during the one or more cardiac cycles, at an implantable pressure sensor (IPS);

generating a pressure signal based on the pressure;

under control of one or more processors configured with executable instructions, analyzing one of the CA or pressure signals, for the one or more cardiac cycles, to detect a candidate arrhythmia;

obtaining an other one of the CA or pressure signals for cardiac cycles corresponding to the one or more cardiac cycles; and confirming or denying the candidate arrhythmia based on the other one of the CA or pressure signals.

17. The method of claim 16, further comprising:

transmitting, from an IMD communications circuit within the IMD, a request for the pressure signals from the IPS;

receiving, at the IMD communications circuit, the pressure signals for the one or more cardiac cycles; and analyzing, under control of the one or more processors housed in the IMD, the pressure signals for the one or more cardiac cycles, to confirm or deny the candidate arrhythmia.

18. The method of claim 16, further comprising:

transmitting, from an IPS communications circuit within the IPS, a request for the CA signals from the IMD;

receiving, at the IPS communications circuit, the CA signals; and analyzing, under control of one or more processors being housed in the IPS, the CA signals for the one or more cardiac cycles, to confirm or deny the candidate arrhythmia.

19. The method of claim 16, further comprising:

comparing the pressure signals, for the one or more cardiac cycles, relative to a template for a normal sinus rhythm to determine when the pressure signals indicate a pressure-indicated arrhythmia; and confirming or denying the candidate arrhythmia based on the comparison of the pressure signals.

20. The method of claim 16, wherein in response to confirming the candidate arrhythmia based on the CA signals and denying the candidate arrhythmia based on the pressure signals, the one or more processors is further configured to increase at least one sensitivity setting associated with sensing the cardiac activity.

* * * * *